US011510576B2

(12) United States Patent
Avitall

(10) Patent No.: US 11,510,576 B2
(45) Date of Patent: Nov. 29, 2022

(54) TREATMENT DEVICE HAVING MULTIFUNCTIONAL SENSING ELEMENTS AND METHOD OF USE

(71) Applicant: Medtronic CryoCath LP, Toronto (CA)

(72) Inventor: Boaz Avitall, Chicago, IL (US)

(73) Assignee: Medtronic CryoCath LP, Toronto (CA)

( * ) Notice: Subject to any disclaimer, the term of this patent is extended or adjusted under 35 U.S.C. 154(b) by 1147 days.

(21) Appl. No.: 15/499,036

(22) Filed: Apr. 27, 2017

(65) Prior Publication Data
US 2018/0310978 A1    Nov. 1, 2018

(51) Int. Cl.
*A61B 5/287*    (2021.01)
*A61B 5/01*    (2006.01)
(Continued)

(52) U.S. Cl.
CPC ................ *A61B 5/01* (2013.01); *A61B 5/053* (2013.01); *A61B 5/0536* (2013.01); *A61B 5/0538* (2013.01); *A61B 5/283* (2021.01); *A61B 5/287* (2021.01); *A61B 5/6853* (2013.01); *A61B 18/02* (2013.01); *A61B 2018/00351* (2013.01);
(Continued)

(58) Field of Classification Search
CPC .. A61B 2018/00351; A61B 2018/0212; A61B 2018/0262; A61B 18/02
See application file for complete search history.

(56) References Cited

U.S. PATENT DOCUMENTS 4,497,181 A    2/1985    Kocher et al.
5,147,355 A    9/1992    Friedman et al.
(Continued)

FOREIGN PATENT DOCUMENTS

CN    105813590 A    7/2016

OTHER PUBLICATIONS

International Search Report and Written Opinion dated Jun. 12, 2018, for corresponding International Application No. PCT/CA2018/050328; International Filing Date: Mar. 19, 2018 consisting of 8 pages.
(Continued)

*Primary Examiner* — Linda C Dvorak
*Assistant Examiner* — Ryan T Clark
(74) *Attorney, Agent, or Firm* — Michael Best & Friedrich LLP

(57) ABSTRACT

A device, system, and method for treating an area of tissue and evaluating lesion formation and quality. The system may include a medical device having a plurality of mapping electrodes on a treatment element, the plurality of mapping electrodes being configured to record from the area of tissue at least one of unipolar impedance measurements, bipolar impedance measurements, local electrical activity, and pace threshold measurements before, during, and after circulation of the cryogenic fluid within the treatment element. These measurements may be transmitted to a control unit having processing circuitry configured to compare pre-treatment measurements, in-treatment measurements, and/or post-treatment measurements to each other and/or to threshold values to determine occlusion and/or lesion quality, such as lesion transmurality.

17 Claims, 8 Drawing Sheets

(51) Int. Cl.
  *A61B 18/02* (2006.01)
  *A61B 5/053* (2021.01)
  *A61B 5/00* (2006.01)
  *A61B 5/0536* (2021.01)
  *A61B 5/0538* (2021.01)
  *A61B 5/283* (2021.01)
  *A61B 18/00* (2006.01)

(52) U.S. Cl.
  CPC .............. *A61B 2018/00357* (2013.01); *A61B 2018/00375* (2013.01); *A61B 2018/00642* (2013.01); *A61B 2018/00791* (2013.01); *A61B 2018/00797* (2013.01); *A61B 2018/00839* (2013.01); *A61B 2018/00863* (2013.01); *A61B 2018/00875* (2013.01); *A61B 2018/0212* (2013.01); *A61B 2018/0262* (2013.01); *A61B 2505/05* (2013.01); *A61B 2562/046* (2013.01)

(56) References Cited

U.S. PATENT DOCUMENTS

| | | | |
|---|---|---|---|
| 5,733,280 | A | 3/1998 | Avitall |
| 6,235,018 | B1 | 5/2001 | LePivert |
| 6,731,225 | B2 | 5/2004 | Vopat |
| 6,981,382 | B2 | 1/2006 | Lentz et al. |
| 7,070,594 | B2 | 7/2006 | Sherman |
| 7,357,797 | B2 | 4/2008 | Ryba |
| 11,051,868 | B2 * | 7/2021 | Avitall .................. A61B 18/02 |
| 2002/0143326 | A1 | 10/2002 | Foley et al. |
| 2006/0155267 | A1 | 7/2006 | Berzak et al. |
| 2008/0200829 | A1 | 8/2008 | Abboud et al. |
| 2012/0035601 | A1 * | 2/2012 | Wittenberger ......... A61B 18/02 606/21 |
| 2012/0143177 | A1 | 6/2012 | Avitall |
| 2012/0191080 | A1 | 7/2012 | Markowitz |
| 2012/0191081 | A1 | 7/2012 | Markowitz |
| 2014/0276710 | A1 * | 9/2014 | Wittenberger ......... A61B 18/02 606/24 |
| 2014/0276712 | A1 | 9/2014 | Mallin et al. |
| 2014/0358140 | A1 * | 12/2014 | Emmons ................ A61N 7/022 606/33 |
| 2015/0119868 | A1 | 4/2015 | Lalonde et al. |
| 2015/0157382 | A1 * | 6/2015 | Avitall ................... A61B 18/02 606/21 |
| 2016/0287136 | A1 | 10/2016 | Condie et al. |

OTHER PUBLICATIONS

European Patent Office, Supplementary European Search Report for corresponding EP Application No. 18 790 308.2, dated Nov. 17, 2020, 8 pages.

China National Intellectual Property Administration First Office Action for Application No. 201880028151.4 dated Feb. 16, 2022 (14 pages including English translation).

China National Intellectual Property Administration Second Office Action for Application No. 201880028151.4 dated Jul. 20, 2022 (14 pages including English translation).

* cited by examiner

TREATMENT DEVICE HAVING MULTIFUNCTIONAL SENSING ELEMENTS AND METHOD OF USE

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a method and system for treating an area of tissue and evaluating lesion formation and quality.

BACKGROUND

Cardiac arrhythmia, a group of disorders in which the heart's normal rhythm is disrupted, affects millions of people. Certain types of cardiac arrhythmias, including ventricular tachycardia and atrial fibrillation, may be treated by ablation (for example, radiofrequency (RF) ablation, cryoablation, microwave ablation, and the like), either endocardially or epicardially.

The effectiveness of an ablation procedure may largely depend on the quality of contact between the treatment element of the medical device and the cardiac tissue. However, proper positioning of the treatment element and achieving good contact between the treatment element and the tissue may be challenging. Further, the effectiveness of the ablation procedure may also depend on whether the lesion is transmural, meaning it extends all the way through the tissue being treated. However, it can be difficult to determine when the lesion has become transmural and to stop the ablation procedure before collateral or non-target tissues are affected. Likewise, it can be difficult to know how long an ablation procedure must continue before an adequate lesion has formed.

Some current methods of assessing or monitoring tissue contact may include using impedance measurements to directly monitor the tissue. However, this method may produce inconclusive results, as such data may be difficult to accurately measure. Further, sensors for these characteristics may not be located on an entirety of, or even most of, the treatment element. Therefore using impedance, temperature, pressure, or other such characteristics may not provide useful information about a contact status of the treatment element at enough locations to give a complete indication of tissue contact. Sill other techniques such as pressure monitoring through the guidewire lumen, $CO_2$ monitoring, or the like cannot be used to pinpoint the exact location of inadequate tissue contact in real time.

Additionally, procedures such as pulmonary vein isolation (PVI) are commonly used to treat atrial fibrillation. This procedure generally involves the use of a cryogenic device, such as a catheter, which is positioned at the ostium of a pulmonary vein (PV) such that any blood flow exiting the PV into the left atrium (LA) is completely blocked. Once in position, the cryogenic device may be activated for a sufficient duration to create a desired lesion within myocardial tissue at the PV-LA junction, such as a PV ostium. If a cryoballoon is used as the treatment element of the cryogenic device, the balloon is typically inflated using a very low temperature liquid gas, enabling the balloon to create a circumferential lesion about the ostium and/or antrum of the PV to disrupt aberrant electrical signals exiting the PV.

The success of this procedure depends largely on the quality of the lesion(s) created during the procedure and whether the cryoballoon has completely occluded the PV. For example, a complete circumferential lesion is produced only when the cryoballoon has completely occluded the PV. Incomplete occlusion allows blood to flow from the PV being treated, past the cryoballoon, and into the left atrium of the heart. This flow of warm blood may prevent the cryoballoon from reaching temperatures low enough to create permanent lesions in the target tissue. The creation of reversible lesions may not be sufficient to achieve electrical isolation and, as a result, atrial fibrillation may be likely to reoccur. Additionally, even if the PV is completely occluded, suboptimal operation of the cryoablation system may result in cryoballoon temperatures that are not low enough, or not applied for a sufficient amount of time, to create permanent lesions in the target tissue.

Current methods of assessing or monitoring PV occlusion include fluoroscopic imaging of radiopaque contrast medium injected from the device into the PV. If the device, such as a cryoballoon catheter, has not completely occluded the PV ostium, some of the contrast medium may flow from the PV into the left atrium. In that case, the device may be repositioned and more contrast medium injected into the PV. This method not only necessitates the use of an auxiliary imaging system, but it also exposes the patient to potentially large doses of contrast medium and radiation. Alternatively, pressure measurement distal to the occlusion site can be used to assess occlusion prior to initiating the coolant injection. Other methods may involve the use of temperature sensors to determine the temperature within the cryoballoon and to correlate the measured temperature to a predicted thickness of ice created in tissue that is in contact with the cryoballoon. However, it may be difficult to accurately determine ice thickness based on balloon temperature alone and this latter method can only be used during injection freeze cycle.

SUMMARY

The present invention advantageously provides a method and system for treating an area of tissue and evaluating lesion formation and quality. In one embodiment, a medical system for treating an area of tissue includes: a medical device including a treatment element and a plurality of mapping elements on the treatment element; and a control unit including: a cryogenic fluid source in fluid communication with the treatment element, circulation of the cryogenic fluid within the treatment element causing formation of an ice ball between the treatment element and the area of tissue; and processing circuitry in electrical communication with the plurality of mapping elements and the plurality of sensors, the processing circuitry being configured to determine transmurality of a lesion based on signals received from the plurality of mapping elements.

In one aspect of the embodiment, the medical device further includes a plurality of sensors on the treatment element, each of the plurality of sensors being associated with at least one of the plurality of mapping elements. In one aspect of the embodiment, each of the plurality of mapping elements includes a corresponding one of the plurality of temperature sensors.

In one aspect of the embodiment, the medical device has a longitudinal axis, the plurality of mapping elements being arranged in a plurality of linear formations, each of the plurality of linear formations being at least substantially parallel to the longitudinal axis. In one aspect of the embodiment, the treatment element has a distal portion and a proximal portion, each of the plurality of linear formations of mapping elements extending between the distal portion and the proximal portion of the treatment element.

In one aspect of the embodiment, the medical device has a longitudinal axis, the plurality of mapping elements being arranged in a plurality of bands, each of the plurality of bands at least partially extending around the longitudinal axis.

In one aspect of the embodiment, the plurality of mapping elements are arranged in clusters of two or more mapping elements.

In one aspect of the embodiment, the plurality of mapping elements are randomly arranged on the treatment element.

In one aspect of the embodiment, each of the plurality of mapping elements is configured to record from the area of tissue at least one of unipolar impedance measurements, bipolar impedance measurements, local electrical activity, and pace threshold measurements before, during, and after circulation of the cryogenic fluid within the treatment element, and each of the plurality of temperature sensors is configured to record temperature measurements before, during, and after circulation of the cryogenic fluid within the treatment element. In one aspect of the embodiment, the processing circuitry is configured to receive recordings from the plurality of mapping elements and to: compare unipolar impedance measurements recorded before the circulation of cryogenic fluid within the treatment element to unipolar impedance measurements recorded after the circulation of cryogenic fluid within the treatment element has ended; determine a thickness of the ice ball between the treatment element and the area of tissue based on the comparison of the unipolar impedance measurements; and correlate the thickness of the ice ball to a lesion quality.

In one aspect of the embodiment, the processing circuitry is further programmed to: compare bipolar impedance measurements recorded before the circulation of cryogenic fluid within the treatment element to bipolar impedance measurements recorded after the circulation of cryogenic fluid within the treatment element has ended; quantify a formation of ice between a pair of treatment elements used to record the bipolar impedance measurements based on the comparison of the bipolar impedance measurements; and correlate the formation of ice to a lesion quality.

In one aspect of the embodiment, the processing circuitry is further programmed to: compare pace threshold measurements recorded before the circulation of cryogenic fluid within the treatment element to pace threshold measurements recorded after the circulation of cryogenic fluid within the treatment element has ended; and determine whether the area of tissue has been ablated based on the comparison.

In one aspect of the embodiment, the processing circuitry is configured to determine that the area of tissue has been ablated when the pace threshold measurements recorded after the circulation of cryogenic fluid within the treatment element has ended are greater than the pace threshold measurements recorded before the circulation of cryogenic fluid within the treatment element by more than a threshold difference.

In one aspect of the embodiment, the processing circuitry is configured to receive recordings from the plurality of mapping electrodes and configured to determine, for each of the plurality of mapping electrodes: that at least a portion of the area of tissue proximate the mapping electrode has been ablated when the mapping electrode records a post-treatment electrogram amplitude value of 0.5 mV or less, the processing circuitry being further configured to determine a lesion surface area based on the post-treatment electrogram amplitude recorded by each of the plurality of mapping electrodes.

In one aspect of the embodiment, the medical device further includes first impedance electrode located immediately adjacent and distal to the treatment element and a second impedance electrode located immediately adjacent and proximal to the treatment element, each of the first and second impedance electrodes having a width of approximately 0.5 mm.

In one aspect of the embodiment, each of the first and second impedance electrodes are configured to record unipolar impedance measurements and bipolar impedance measurements, the processing circuitry further being configured to determine a thickness of the ice ball between the area of tissue and at least the first impedance electrode based on at least one of unipolar and bipolar impedance measurements recorded by at least the first impedance electrode.

In one embodiment, a method of determining lesion transmurality may include: positioning a treatment element of a medical device in contact with an area of tissue, the treatment device being in fluid communication with a source of cryogenic fluid and including a cryoballoon and a plurality of mapping elements on the cryoballoon; recording from the area of tissue at least one of a pre-treatment unipolar impedance measurement, a pre-treatment bipolar impedance measurement, a pre-treatment pace threshold measurement, and pre-treatment electrogram (local electrophysiological activity); transmitting at least one pre-treatment recording to a control unit having processing circuitry; circulating the cryogenic fluid within the cryoballoon to lower the temperature of the cryoballoon to a temperature that is sufficient to ablate tissue; ceasing the circulation of the cryogenic fluid within the cryoballoon; recording from the area of tissue at least one of a corresponding post-treatment unipolar impedance measurement, a post-treatment bipolar impedance measurement, a post-treatment pace threshold measurement, and a post-treatment electrogram amplitude; transmitting the at least one post-treatment measurement to the control unit; comparing the at least one pre-treatment measurement to the at least one post-treatment measurement; and determining lesion transmurality in the area of tissue based on the comparison.

In one aspect of the embodiment, the method further includes before ceasing the circulation of cryogenic fluid within the cryoballoon, recording from the area of tissue at least one of a corresponding in-treatment unipolar impedance measurement, an in-treatment bipolar impedance measurement, an in-treatment electrogram, and an in-treatment pace threshold measurement; and transmitting the at least one in-treatment measurement to the control unit.

In one aspect of the embodiment, the method further includes comparing the at least one in-treatment measurement to at least one of a corresponding pre-treatment measurement and a corresponding post-treatment measurement.

In one aspect of the embodiment, the at least one in-treatment measurement is a unipolar impedance measurement, the at least one of a corresponding pre-treatment measurement and a corresponding post-treatment measurement is a pre-treatment unipolar impedance measurement, the comparing the at least one pre-treatment measurement to the at least one in-treatment measurement includes comparing the pre-treatment unipolar impedance measurement to the in-treatment unipolar measurement, the method further including: establishing at least one of a threshold ice ball thickness; correlating the comparison between the pre-treatment and in-treatment unipolar impedance measurement to an ice ball thickness; and comparing the correlated ice ball thickness to the threshold ice ball thickness, determining lesion transmurality including determining the lesion is transmural when the correlated ice ball thickness is at least equal to the threshold ice ball thickness.

In one aspect of the embodiment, the method further includes automatically ceasing the circulation of cryogenic fluid within the cryoballoon when the transmural lesion is determined to have been created.

In one embodiment, a medical system for treating an area of tissue includes: a medical device including: a treatment element; a plurality of mapping electrodes on the treatment element, each of the plurality of mapping electrodes being configured to record from the area of tissue at least one of unipolar impedance measurements, bipolar impedance measurements, local electrical activity, pace threshold measurements before, during, and after circulation of the cryogenic fluid within the treatment element; a plurality of temperature sensors on the treatment element, each of the plurality of temperature sensors being associated with at least one of the plurality of mapping elements, each of the plurality of temperature sensors being configured to record from the area of tissue temperature measurements before, during, and after circulation of the cryogenic fluid within the treatment element; a first impedance electrode located immediately adjacent and distal to the treatment element, the first impedance electrode including a distal temperature sensor; and a second impedance electrode located immediately adjacent and proximal to the treatment element, the second impedance electrode including a distal temperature sensor, each of the first and second impedance electrodes having a width of approximately 0.5 mm; and a control unit including: a cryogenic fluid source in fluid communication with the treatment element, circulation of the cryogenic fluid within the treatment element causing formation of an ice ball between the treatment element and the area of tissue; and processing circuitry in electrical communication with the plurality of mapping electrodes, the plurality of sensors, the first and second impedance electrodes, and the distal and proximal temperature sensors, the processing circuitry being configured to determine transmurality of a lesion based on signals received from the plurality of mapping electrodes by at least one of: comparing unipolar impedance measurements recorded before the circulation of cryogenic fluid within the treatment element to at least one of unipolar impedance measurements recorded during the circulation of cryogenic fluid within the treatment element and unipolar impedance measurements recorded after the circulation of cryogenic fluid within the treatment element has ended; comparing bipolar impedance measurements recorded before the circulation of cryogenic fluid within the treatment element to at least one of bipolar impedance measurements recorded during the circulation of cryogenic fluid within the treatment element and bipolar impedance measurements recorded after the circulation of cryogenic fluid within the treatment element has ended; comparing pace threshold measurements recorded before the circulation of cryogenic fluid within the treatment element to at least one of pace threshold measurements recorded during the circulation of cryogenic fluid within the treatment element and pace threshold measurements recorded after the circulation of cryogenic fluid within the treatment element has ended; and comparing electrogram amplitude measurements recorded before the circulation of cryogenic fluid within the treatment element to at least one of electrogram amplitude measurements recorded during the circulation of cryogenic fluid within the treatment element and electrogram amplitude measurements recorded after the circulation of cryogenic fluid within the treatment element has ended.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
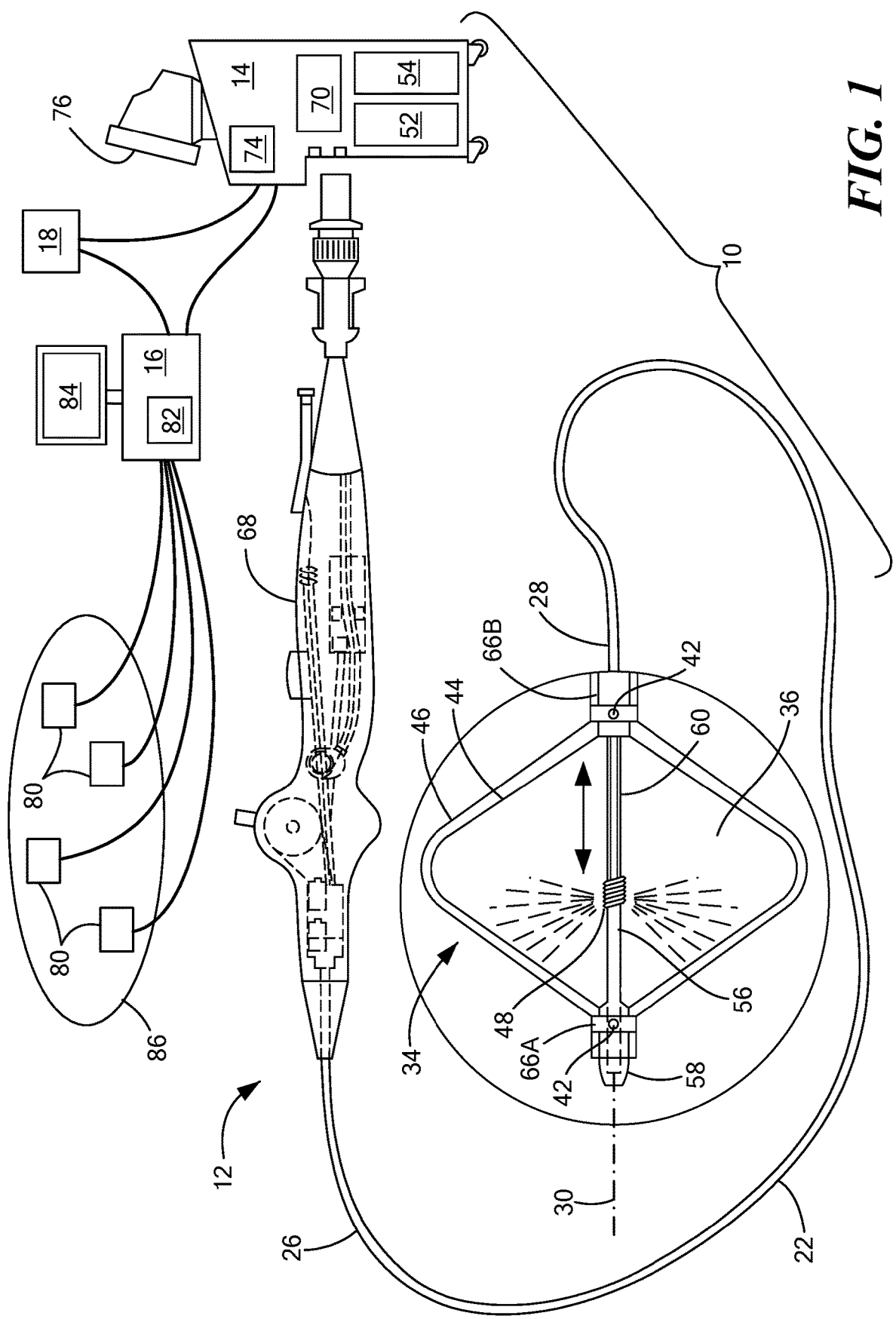
FIG. 1 shows an exemplary medical system.

The devices, systems, and methods described herein may be used to treat tissue and evaluate the resulting lesion. Before describing in detail exemplary embodiments, it is noted the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Referring now to the drawing figures in which like reference designations refer to like elements, an embodiment of a medical system is shown in FIG. 1, generally designated as "10." The system 10 may generally include a treatment device 12, a control unit 14, and a navigation system 16. The system 10 may optionally include an imaging system 18 for obtaining images of anatomical features within a patient.

The treatment device 12 may be a treatment and mapping device. The device 16 may include an elongate body 22 passable through a patient's vasculature and/or proximate to a tissue region for diagnosis or treatment. For example, the device 12 may be a catheter that is deliverable to the tissue region via a sheath or intravascular introducer (not shown) or a device that can access the pericardial space. The elongate body 22 may define a proximal portion 26, a distal portion 28, and a longitudinal axis 30, and may further include one or more lumens disposed within the elongate body 22 thereby providing mechanical, electrical, and/or fluid communication between the elongate body proximal portion 26 and the elongate distal portion 28.

The device 12 may further include one or more treatment elements 34 at, coupled to, or on the elongate body distal portion 28 for energetic, therapeutic, and/or investigatory interaction between the medical device 12 and a treatment site or region. In addition to cryogenic therapy, the treatment region element(s) 34 may also deliver, for example, radiofrequency energy, ultrasound energy, laser energy, or other energetic transfer with a tissue area in proximity to the treatment element(s), including cardiac tissue. For example, the treatment element(s) 34 may include thermally transmissive regions in thermal communication with a coolant or heat source, thermally transmissive regions in electrically communication with a power source, surface therapeutic elements such as surface radiofrequency electrodes, or the like. Additionally, the device 12 may include more than one type of treatment element 34. In the exemplary system embodiment shown in FIG. 1, the device 12 may include an expandable treatment element 34, such as a cryoballoon that is inflated by the circulation of cryogenic fluid within the cryoballoon interior chamber 36. As is discussed below, the treatment element 34 may include a plurality of sensing or mapping electrodes 40.

The expandable treatment element 34 shown in FIG. 1 may include an inner (or first) cryoballoon 44 and an outer (or second) cryoballoon 46. The treatment element 34 may be coupled to a portion of the elongate body distal portion 28. The treatment element 34 may further include one or more material layers providing for puncture resistance, radiopacity, or the like. If the device 12 may also include one or more fluid injection elements 48 in fluid communication with a source of cryogenic fluid for delivering the cryogenic fluid 52 to the interior chamber 36 of the treatment element 34. The interior chamber 36 may be defined by the inner cryoballoon 44. The inner 44 and outer 46 cryoballoons may define an interstitial space therebetween, which may optionally also be in fluid communication with a source of cryogenic fluid 52 in or otherwise associated with the control unit 14. To facilitate cryogenic fluid delivery to and recovery from the treatment element 34, the device and system may include one or more fluid flow paths between the source of cryogenic fluid 52 and the treatment element 34. For example, the device 12 may include a fluid delivery conduit and a fluid recovery conduit within the elongate body 22, which are in fluid communication with the source of cryogenic fluid 52 and a cryogenic fluid recovery reservoir 54 or other scavenging or recovery system.

The treatment element 34 may be coupled to a portion of the elongate body distal portion 28. The device may optionally include a shaft 56 that is slidably disposed within the elongate body 22 and at least a portion of the shaft 56 may be located within the interior chamber 36 of the treatment element 34. The shaft 56 may include or define a distal tip 58 that may protrude beyond the distal end of the treatment element 34. Retraction and extension (that is, longitudinal movement of) the shaft 56 within the elongate body 22 may affect the size and shape of the cryoballoons 44, 46. The fluid injection element 48 may be in fluid communication with or may be defined by a portion of a fluid delivery conduit 60 within the interior chamber 36. As a non-limiting example, a portion of the fluid delivery conduit 60 may be wrapped around a portion of the shaft 56 within the interior chamber 36. The shaft 56 may further include a guidewire lumen 62 through which a guidewire 64 may be extended during a procedure. As a non-limiting example, the guidewire 64 may extend out a distal opening of the guidewire lumen 62, and distal to the treatment element 34, into a pulmonary vein, while the treatment element 34 is used to ablate or map tissue on the left atrial wall. The guidewire 64 may be steerable and may bear one or more sensors and/or mapping electrodes (not shown). Further, the guidewire lumen 62 may be used to deliver cold saline solution to a location that is distal to the treatment element for PV occlusion assessment. As a non-limiting example, the control unit 14 may include a saline reservoir in fluid communication with the guidewire lumen 62, or other portion of the device 12, for delivery of cold saline solution to a location that is distal to the treatment element, such as within a PV. As is discussed in more detail below, the cold saline may be used to cause temperature changes detected by the device 12 that can be used to assess ice formation and/or PV occlusion.

The treatment element 34 may include a plurality of mapping elements. As a non-limiting example, the device 12 may include a plurality of mapping electrodes 40 coupled to, integrated with, or embedded within the material of the outer cryoballoon 46. The plurality of electrodes 40 may be configured for both mapping and the delivery of treatment energy. Further, the plurality of electrodes 40 may also be configured to record impedance measurements from the tissue for lesion assessment and each may be associated with one or more sensors 42, such as a temperature sensor, as discussed in greater detail below. For example, each mapping electrode 40 and, optionally, treatment element in communication with a power source may be electrically conductive segments for conveying an electrical signal, current, or voltage to a designated tissue region and/or for measuring, recording, receiving, receiving, assessing, or otherwise using one or more electrical properties or characteristics of surrounding tissue or other electrodes. Further, the mapping electrodes 40 may be in wireless or wired communication with the control unit 14. The electrodes may be configured in a myriad of different geometric configurations or controllably deployable shapes, and may also vary in number to suit a particular application, targeted tissue structure or physiological feature.

The device 12 may further include one or more electrodes 66 that are used for measuring impedance signals, and may be referred to herein as impedance electrodes. However, the impedance electrodes 66 may also be used by the navigation system 16 to visualize the device 12 on a control unit display and/or navigation system display. For example, the device 12 may include a first impedance electrode 66A immediately adjacent and distal to the expandable portion of the treatment element 34 and a second impedance electrode 66B immediately adjacent and proximal to the expandable portion of the treatment element 34. Additionally, each impedance electrode 66 may include or be associated with a thermocouple or other temperature sensor 42, such that impedance and temperature measurements may be recorded at the location of each impedance electrode 66. In one embodiment, the second or proximal impedance electrode 66B includes a temperature sensor 42. In another embodiment, the second or proximal impedance electrode 66B does not include a temperature sensor 42. Further, the navigation system 16 may receive data from the mapping electrodes 40 to generate a map of at least a portion of the heart (or other treatment location), on which areas of lesion formation and/or the device location may be displayed.

As discussed below, the combination of impedance electrodes 66 and temperature sensors 42 allows for evaluation of occlusion of a hollow anatomical feature, such as a pulmonary vein, by the treatment element 34 without necessitating the use of renal toxic dye. For example, the treatment element 34 may be positioned at a PV ostium, such as in a position believed to occlude the PV. Cold saline may be delivered into the PV, distal to the device 12 (for example, through the guidewire lumen 62) and temperature measurements by the thermocouple to other temperature sensor 42 on or associated with the first or distal impedance electrode 66A may be used to evaluate ice formation and/or temperature of the blood within the PV (for evaluation of occlusion of the PV). Further, the impedance electrodes 66 may be sized and located to optimize and enhance the accuracy of impedance recording. As a non-limiting example, the first impedance electrode 66A may be immediately distal to the treatment element 34, such as the inflatable or expandable portion 67 of the cryoballoons 44, 46 (as shown in FIG. 1). Likewise, the second impedance electrode 66B may be immediately proximal to the treatment element 34, such as the inflatable or expandable portion 67 of the cryoballoons 44, 46. In fact, each of the first 66A and second 66B impedance electrodes may be so close to the inflatable or expandable portion 67 of the treatment element that they are in contact with at least a portion of a distal face and at least a portion of a proximal face of the treatment element 34, respectively, when the treatment element 34 is inflated or expanded. The proximity of the impedance electrodes 66A, 66B to the treatment element 34 may minimize or negate the chance the impedance electrodes 66A, 66B record non-target or interference impedance measurement (that is, impedance measurements that are irrelevant to the evaluation of ice formation and/or ice thickness).

Further, the combination of impedance electrodes 66 and temperature sensors 42 allows the system 10 to generate an anatomical map(s) of a target treatment location(s), such as a heart, by 3D navigation. The combination also allows the system 10 to generate electrophysiological 3D activation and electrogram amplitude map(s), which can then be superimposed on the anatomical map(s).

Although not shown, the system 10 may include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

The medical device 12 may include a handle 68 coupled to the elongate body proximal portion 26. The handle 68 may include circuitry for identification and/or use in controlling of the medical device 12 or another component of the system. Additionally, the handle 68 may also include connectors that are mateable to the control unit 14 to establish communication between the medical device 12 and one or more components or portions of the control unit 14. The handle 68 may also include one or more actuation or control features that allow a user to control, deflect, steer, or otherwise manipulate a distal portion of the medical device 12 from the proximal portion of the medical device 12. For example, the handle 68 may include one or more components such as a lever or knob for manipulating the elongate body 22 and/or additional components of the medical device 12.

As used herein, the term "control unit 14" for simplicity may include any system components that are not part of the medical device 12 itself, other than components of the navigation system 16 and the imaging system 18 (if included), regardless of whether the component is physically located within or external to the control unit 14. Further, the navigation system 16 may be a standalone system in communication with the control unit 14 or may be contained within or integrated with the control unit 14, even though it is shown as being physically separated from the control unit in FIG. 1. The control unit 14 may include one or more components for the delivery of one or more energy modalities for which the system is used. For example, the control unit 14 may include a source of cryogenic fluid 52, an exhaust or scavenging system for recovering or venting expended fluid for re-use or disposal, which may include a cryogenic fluid recovery reservoir 54, as well as various control mechanisms. In addition to providing an exhaust function for the source of cryogenic fluid 52, the control unit 14 may also include pumps, valves, controllers or the like to recover and/or re-circulate fluid delivered to the handle 68, the elongate body 22, and/or the fluid pathways of the device 12. Further, a vacuum pump in the control unit 14 may create a low-pressure environment in one or more conduits within the medical device 12 so that fluid is drawn into the conduit(s)/lumen(s) of the elongate body 22, away from the distal portion 28 and towards the proximal portion 26 of the elongate body 22. Additionally or alternatively, the control 14 unit may include an energy source 70 as a treatment or diagnostic mechanism in communication with the treatment element(s) 34 of the device 12. As a non-limiting example, the energy source 70 may be a radiofrequency generator having a plurality of output channels, and it may be operable in one or more modes of operation (for example, unipolar mode and/or bipolar mode).

The control unit 14 may further include processing circuitry 74 that may include one or more controllers, processors, and/or software modules configured to execute instructions or algorithms to provide for the automated operation and performance of the features, sequences, calculations, or procedures described herein and/or required for a given medical procedure. In one embodiment, the processing circuitry may include a processor and a memory. The memory may be in electrical communication with the processor and have instructions that, when executed by the processor, configure the processor to receive, process, or otherwise use signals from the device 12. Further, the control unit 14 may include one or more user input devices, controllers, and displays 76 for collecting and conveying information from and to the user.

The system 10 may include a navigation system 16, which may be any commercially available navigation system suitable for use with the control unit 14, device 12, and type of procedure. As a non-limiting example, the navigation system 12 may include a plurality of surface electrodes 80, a reference electrode (not shown), and processing circuitry 82 that collects and processes signals from the device mapping electrodes 40, and a display 84 that displays to the user the location of the device 12 within the patient's body and/or relative to the target anatomical feature, recommended treatment areas, tissue thickness, or the like. The processing circuitry 82 may include a memory and a processor, the memory in communication with the processor and having instructions that, when executed by the processor, configure the processor to perform the calculations and determinations discussed herein. The navigation system 12 may also include an energy source (not shown) for delivering energy to the plurality of surface electrodes 80. Alternatively, the navigation system 12 may be in communication with the control unit energy source 70. For example, the processing circuitry 82 may be configured, programmed, or programmable to perform the calculations and make the determinations discussed in greater detail below to identify an anatomical feature and/or a target location for a medical device. Further, the processing circuitry 82 may execute software and display a software interface with which the user may interact to make a selection, rotate and flag an image, open folders, control the navigation system 12, or the like. As a non-limiting example, the user may interact with the software interface using a touch screen, a keyboard, a mouse, or other input device.

The surface electrodes 80 may be applied to the patient's 86 skin and may deliver relatively low-frequency radiofrequency energy through the patient toward the procedure site, current device location, or the target anatomical feature. The mapping electrodes 40 on the device 12 may each record a voltage and impedance from this energy and transmit data to the processing circuitry 82, which may then determine a position of the impedance electrodes 66, and therefore the device 12, within the patient 86 (in this sense, the impedance electrodes 66 may function as navigation electrodes). In addition to impedance-based systems, other navigation electrodes may be used such as magnetic field based, hybrid impedance/magnetic field based, ultrasound field based, and/or radiation based, and/or navigation systems that may be developed in the future. The processing circuitry 82 may perform this calculation many times during a procedure, frequently updating the registered location and displaying such to the user so the user can visualize the location of the device relative to the target anatomical feature and tissue electrical activity in the target anatomical feature in real time.

The system 10 may optionally include an imaging system 18, such as an ultrasound system. The imaging system 18 may be in communication with and digitally transmit images to the navigation system 16 and/or the control unit 14 for further processing. Alternatively, images recorded by the imaging system 18 may be recorded and transferred to the navigation system 16 and/or the control unit 14 by a user.

Figure 2:
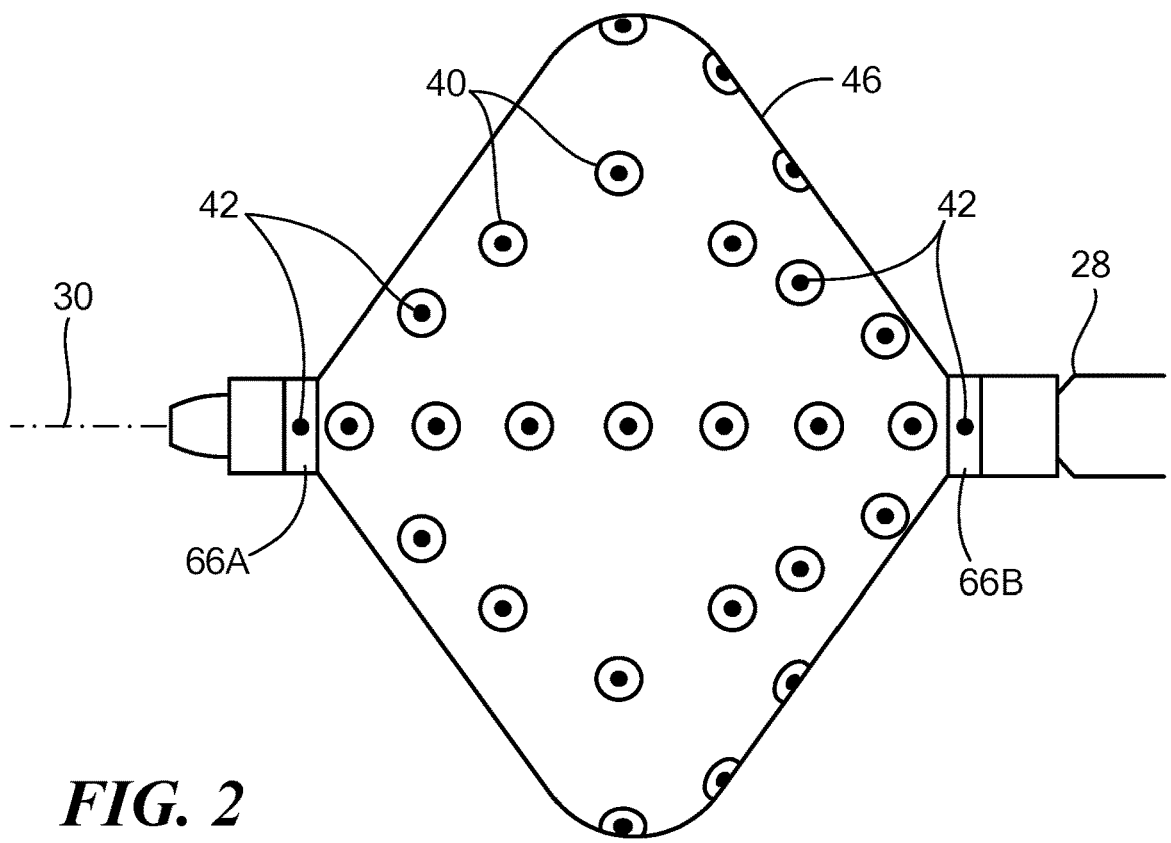
FIG. 2 shows a close-up view of a distal portion of the medical device shown in FIG. 1 having a first configuration of mapping elements.

Referring now to FIGS. 2-5, the distal portion of an exemplary medical device is now described in more detail. As noted above, the device 12 may include one or more treatment elements 34, a plurality of mapping electrodes 40, and one or more impedance electrodes 66. FIG. 1 shows a cross-sectional view of the treatment element 34, and therefore the mapping electrodes 40 are not shown. FIG. 2 shows the distal portion of the medical device 12 of FIG. 1, with the mapping electrodes 40 shown. Each mapping electrode 40 and impedance electrode 66 may be composed of a thermally and/or electrically conductive material, such as a metal, metal alloy, or other suitable biocompatible conductive material. As a non-limiting example, this conductive material may be incorporated into, implanted into, integrated with, and/or deposited on the outer cryoballoon 46 in the areas where the mapping electrodes 40 are located. As a further non-limiting example, the mapping electrodes 40 may be mechanically coupled to an outer surface of the outer cryoballoon 46, such as through the use of adhesives, chemical bonding, or other suitable means of attachment, as may be the case if the mapping electrodes 40 are components such as typical band electrodes. The impedance electrodes 66 and/or temperature sensors 42 may be likewise attached to the elongate body 22 and/or the treatment element 34.

Figure 3:
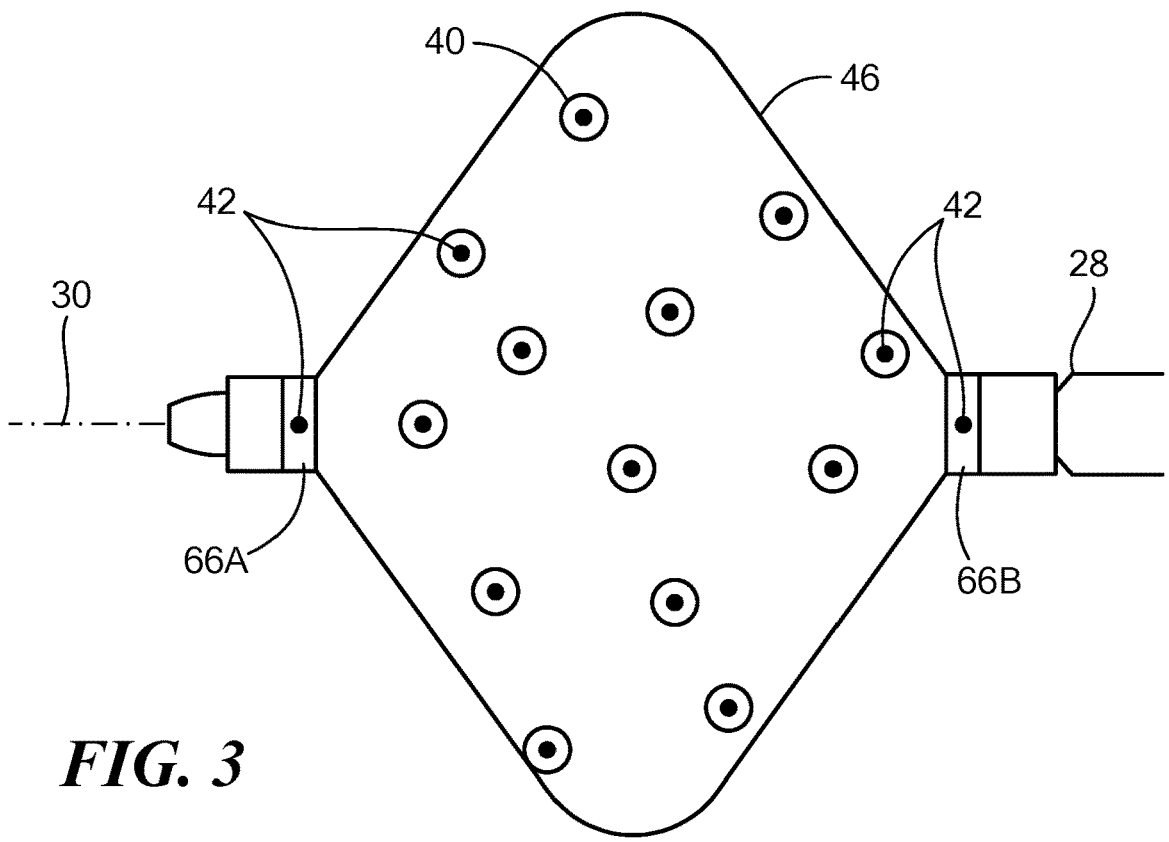
FIG. 3 shows a close-up view of a distal portion of the medical device shown in FIG. 1 having a second configuration of mapping elements.
Figure 4:
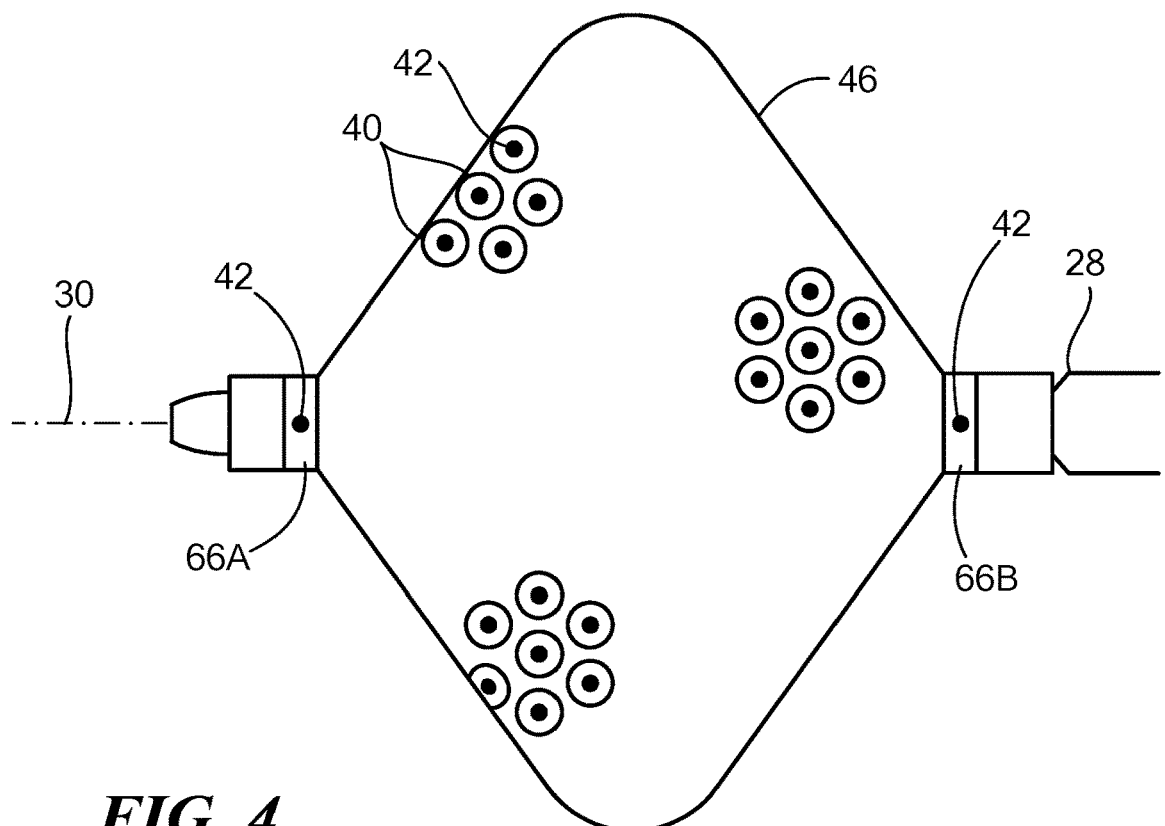
FIG. 4 shows a close-up view of a distal portion of the medical device shown in FIG. 1 having a third configuration of mapping elements.
Figure 5:
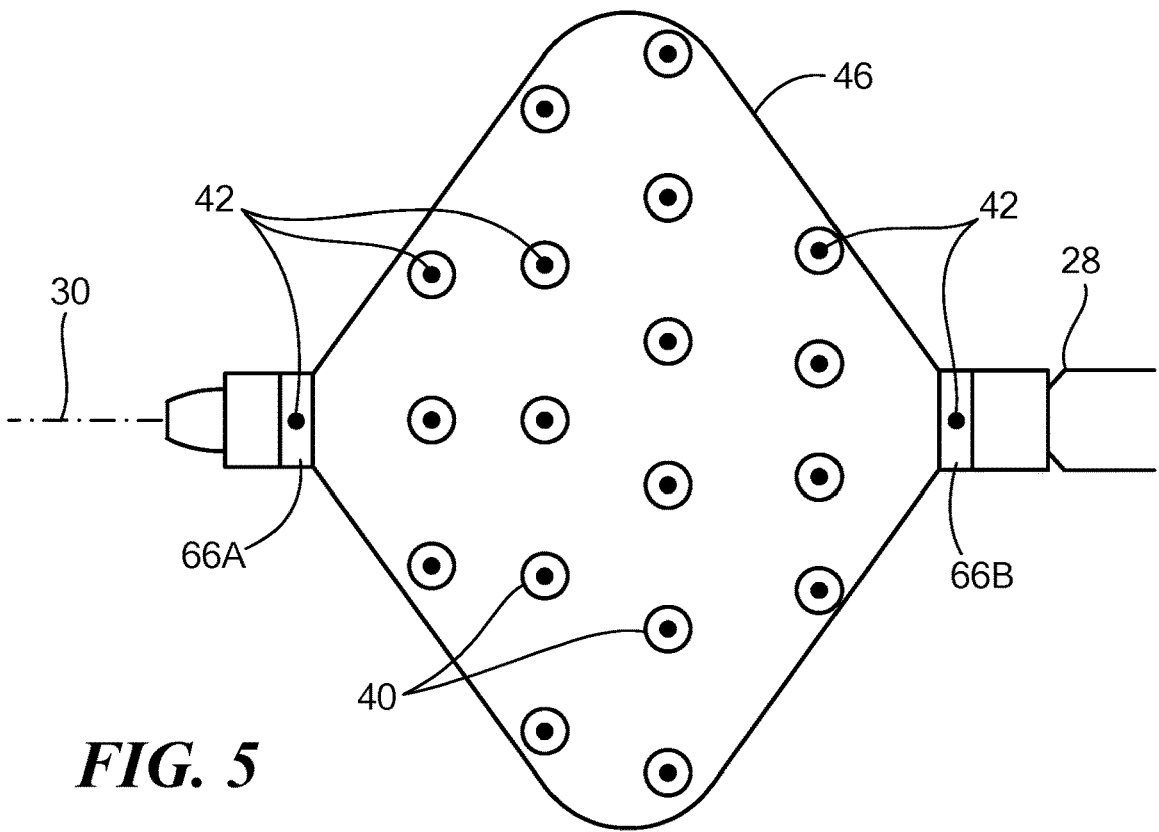
FIG. 5 shows a close-up view of a distal portion of the medical device shown in FIG. 1 having a fourth configuration of mapping elements.

In the configuration shown in FIG. 2, the mapping electrodes 40 may be arranged in a plurality of linear formations that extend between the distal end and the proximal end of the outer cryoballoon 46, or at least that portion of the outer cryoballoon 46 that is not coupled to the shaft 56 or elongate body distal portion 28. The lines of mapping electrodes 40 may be at least substantially parallel to the device longitudinal axis 30 (that is, the lines may be parallel except for slight or insignificant variations in mapping electrode positioning, such as those that may be made during device manufacture). Although the mapping electrodes 40 are shown as being neatly arranged in FIG. 2, it will be understood that the mapping electrodes 40 may alternatively be at scattered locations on the cryoballoon 46 in any pattern (for example, the mapping electrodes 40 may be randomly spaced, as shown in FIG. 3). Further, the mapping electrodes 40 may be arranged in configurations other than that shown in FIG. 2, such as in clusters of two or more mapping electrodes 40 (for example, as shown in FIG. 4), bands that extend around the circumference of the cryoballoon 46 at several locations (for example, as shown in FIG. 5), or in other patterns. In the embodiment shown in FIG. 5, each band of mapping electrodes 40 may at least partially extend around the longitudinal axis 30, rather than being parallel to it. In other words, the mapping electrodes 40 may be radially arranged about the longitudinal axis at a plurality of locations along the longitudinal axis.

Each mapping electrode 40 may include or be associated with one or more sensors 42. Alternatively, each sensor 42 may be associated with one or more mapping electrodes 40. For example, one or more sensors 42 may be coupled to, integrated with, or located immediately proximate each mapping electrode 40. The one or more sensors 42 may be configured to record data such as temperature, pressure, electrograms, or other data.

In one embodiment, the first impedance electrode 66A and its temperature sensor 42 may be immediately distal to the treatment element 34, such as the inflatable or expandable portion 67 of the cryoballoons 44, 46 (as shown in FIG. 1). Likewise, the second impedance electrode 66B may be immediately proximal to the treatment element 34, such as the inflatable or expandable portion 67 of the cryoballoons 44, 46. In fact, each of the first 66A and second 66B impedance electrodes may be so close to the inflatable or expandable portion 67 of the treatment element that they are in contact with at least a portion of a distal face and at least a portion of a proximal face of the treatment element 34, respectively, when the treatment element 34 is inflated or expanded. The proximity of the impedance electrodes 66A, 66B to the treatment element 34 may maximize the sensitivity of the electrodes 66A, 66B to record ice formation on the surface of the treatment element 34.

Additionally, each of the impedance electrodes 66A, 66B may have a width of approximately 0.5 mm (±0.1 mm) or less. Thus, the impedance electrodes 66 are relatively small (for example, as compared to band electrodes used in currently known systems). This size, and the position of the impedance electrodes 66 immediately adjacent to (and in some embodiments in contact with) the treatment element 34, enhances impedance measurement accuracy. Further, each impedance electrode 66A, 66B may also include or be associated with a thermocouple or other sensor 42, such as a pressure sensor, temperature sensor, or any other suitable sensor for recording tissue characteristics of interest.

Figure 6:
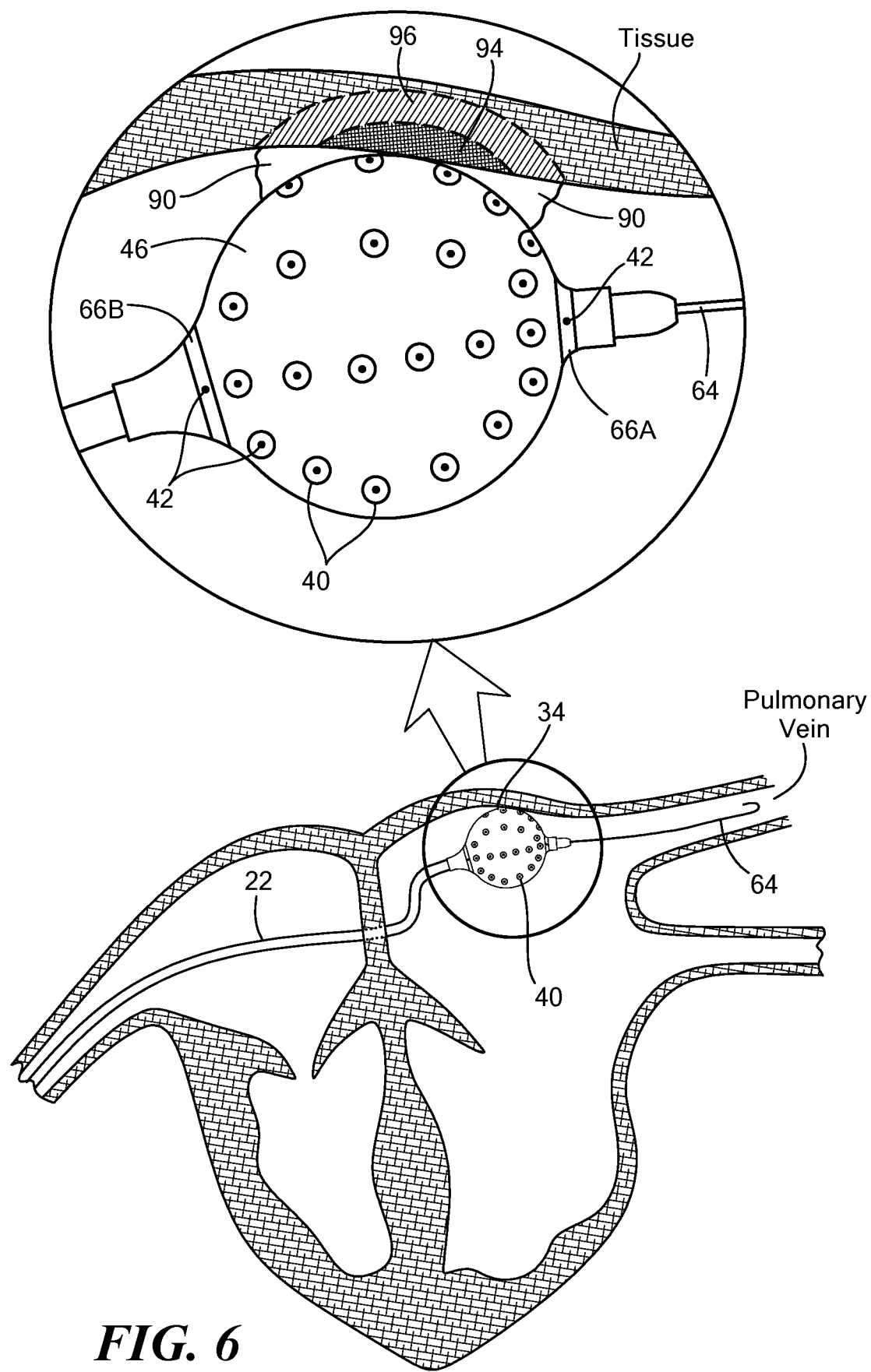
FIG. 6 shows a treatment element of the medical device in contact with a target area of tissue.
Figure 7:
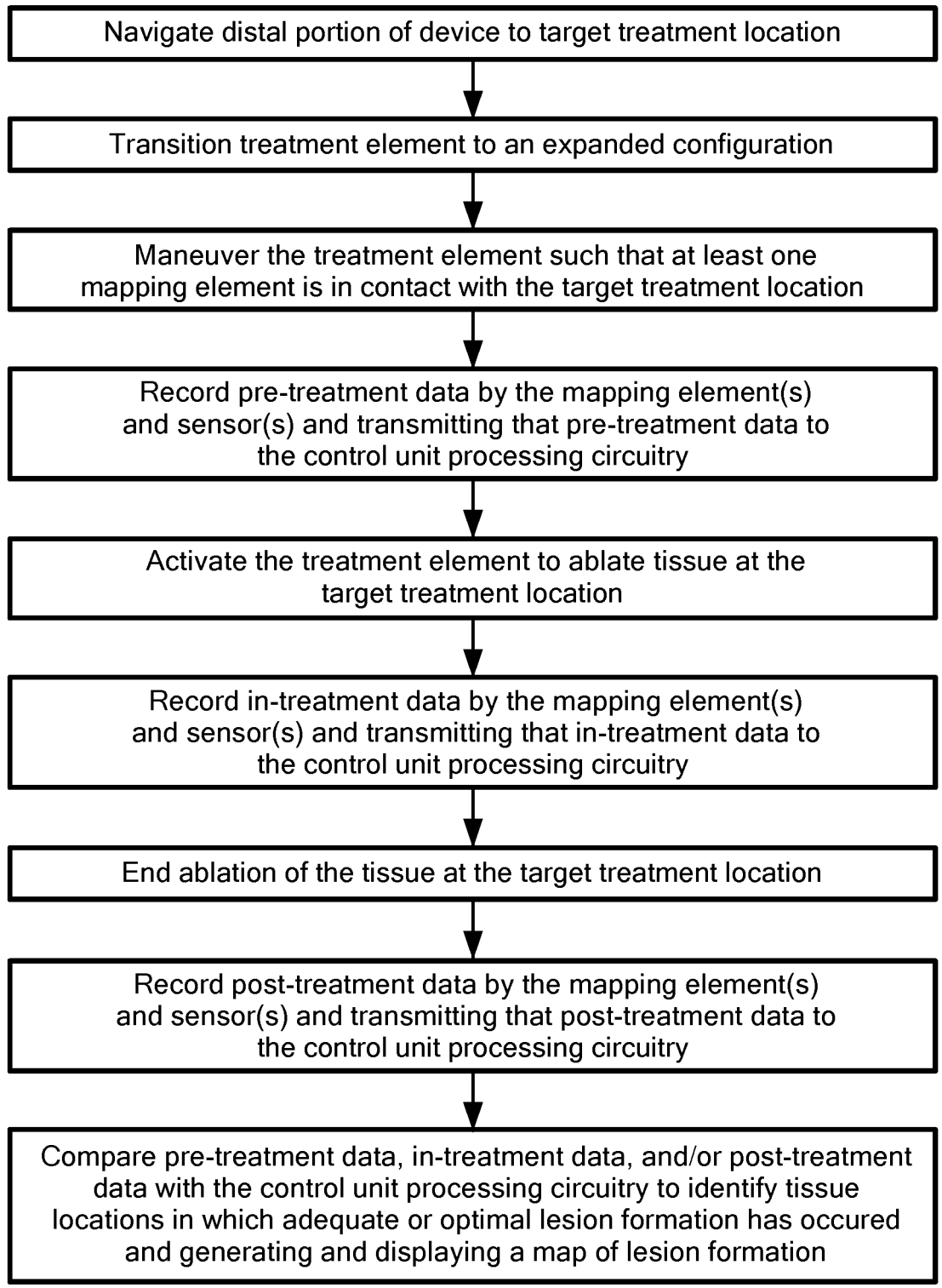
FIG. 7 shows an exemplary method of use of a medical device having a plurality of mapping elements

Referring now to FIGS. 6 and 7, an embodiment of a medical device positioned at a target location and a method of using the device are shown. In a first step 110, the distal portion 28 of the device 12 may be navigated to a target treatment location, such as within a chamber of the heart. The treatment location may be accessed through a femoral, radial, or brachial location. In a second step 120, the treatment element 34 may be transitioned from an at least substantially linear first configuration to an expanded second configuration. For example, cryogenic fluid may be delivered from the source of cryogenic fluid through the fluid delivery conduit 60, fluid injection element 48, and into the interior chamber 36 to inflate the inner 44, and expand the outer 46, cryoballoon (this expansion of the outer cryoballoon 46 may also be referred to as inflating the outer cryoballoon 46). In a third step 130, the expanded treatment element 34 may be maneuvered or positioned such that at least one of the plurality of mapping electrodes 40 is in contact with a target treatment location. The user may use position information from the impedance electrodes 66 and/or the imaging system 18 to assist with placement of the treatment element 34. For example, a lateral surface of the treatment element 34 may be used to record data from tissue with which the treatment element 34 is in contact.

The mapping electrodes 40 may be used for anatomical high-resolution chamber definition (such as by collecting high-density anatomical and electrical activity from the tissue), high-fidelity electrical activation mapping and electrical amplitude determination of the cardiac chamber, pacing and pace threshold determination, rapid activation maps, and electrical activity amplitude maps (such as by recording electrical activity throughout the heart by moving the treatment element 34 relative to the cardiac tissue), pre-treatment, in-treatment, and post-treatment tissue impedance determination to define tissue viability, ice formation and thickness determinations, and post-treatment efficacy. Additionally, the treatment element 34 may be used for not only cryoablation, but also for cold mapping.

In a fourth step 140, pre-treatment data may be recorded by and transmitted from the mapping electrode(s) 40 and sensor(s) 42 to the control unit processing circuitry 74 for further processing and communication to the user. This pre-treatment data may provide baseline or threshold values to which in-treatment and post-treatment data may be compared to evaluate treatment efficacy. For example, the mapping electrodes 40 may be configured to record pre-treatment tissue impedance, pre-treatment local electrical activity, and pre-treatment pace threshold. The mapping electrodes 40 may operate as a unipolar and bipolar electrode array, configured to record local electrograms (unipolar and/or bipolar), a unipolar pace threshold, and impedance (unipolar and/or bipolar). Likewise, the sensors 42 may be configured to record pre-treatment temperature measurements.

Pace threshold is the minimum amount of pulsed current (for example, pulses having a 0.5 msec duration) that results in activation of electrical activity in the cardiac tissue, such as myocardial tissue. During unipolar pacing energy delivery, the pulses may be delivered through a designated mapping electrode 40 (electrode) on the treatment element 34 to a surface electrode 80 on the patient's skin (for example, the surface electrode may be attached to the patient's leg). Before the circulation of cryogenic fluid within the treatment element, (that is, pre-treatment or pre-ablation), the pace threshold is typically low, such as between 1-2 mA, whereas the pace threshold may be above 20 mA after the circulation of cryogenic fluid within the treatment element has ended (post-treatment). This increase indicates that the excitable tissues have been destroyed.

Unipolar impedance is a measure of the electrical resistance path between a mapping electrode 40 (electrode) in contact with cardiac muscle and a reference or surface electrode on the patient's skin. Unipolar impedance measurements may be used to measure the thickness of the ice ball between the treatment element 34 and the tissue. Bipolar impedance, on the other hand, is a measure of the electrical resistance path between two mapping electrodes 40 (electrodes), such as two adjacent mapping electrodes 40. Bipolar impedance measurements may be used to determine or quantify how much ice has built up between the two mapping electrodes 40, and between other pairs of mapping electrodes 40, used to record the bipolar impedance measurements. In general, this determination is most accurate if the mapping electrodes 40 are within approximately 5 mm of each other.

In a fifth step 150, the treatment element 34 may be activated to ablate the target tissue. For example, the target tissue may be cryoablated by circulating cryogenic fluid through the treatment element 34 to cool the outer cryoballoon 46 to a temperature sufficient to ablate tissue with which it is in contact. Additionally, if the device 12 includes one or more treatment elements in addition to the cryoballoons 44, 46, the device 12 may also be used to ablate the target tissue through one or more energy modalities, such as by delivering radiofrequency energy, ultrasound energy, laser energy, or by other energetic transfer with the tissue.

In a sixth step 160, in-treatment data may be collected by the mapping electrodes 40 and sensors 42 while the treatment element(s) 34 is activated and ablating the target tissue, and this data may be transmitted from the mapping electrode(s) 40 and sensors 42 to the control unit processing circuitry 74 for further processing and communication to the user. For example, the mapping electrodes 40 may record high-resolution impedance measurements and the sensors 42 may record temperature measurements, impedance measurements, electrogram amplitude measurements, or the like from the tissue. These measurements may then be transmitted to the control unit 14, where the processing circuitry 74 may process or use them to determine the size (surface area) of the tissue lesion created by the treatment, areas of sufficient lesion formation, and/or a thickness of ice formation. As the outer cryoballoon 46 is cooled to ablate the tissue, ice 90 from freezing blood surrounding the treatment site may form between the cryoballoon 46 and the tissue and cryoadhere the treatment element 34 to the tissue. This ice 90 may contribute to lesion formation; therefore, assessment of the thickness of the ice may provide an indication of lesion quality and treatment efficacy. For example, the processing circuitry may establish a threshold ice thickness that indicates lesion transmurality in the particular area of tissue being treated, such as by using a data table of empirical evidence or historical data for a particular patient. As ice thickness increases, the mapping electrodes 40 may detect a rise in impedance and the sensors 42 may detect a decrease in temperature.

In a seventh step 170, circulation of cryogenic fluid within the treatment element 34 may be stopped, either manually or automatically by the system 10, in order to end the ablation of the tissue, allow the ice 90 to thaw, and to break cryoadhesion between the treatment element (i.e. the cryoballoon 46) and the tissue. In an eighth step 180, post-treatment data may be transmitted from the mapping electrode(s) 40 and the sensors 42 to the control unit processing circuitry 74 for further processing and communication to the user. Post-treatment data may include, but is not limited to, unipolar pace threshold, bipolar pace threshold, unipolar impedance, bipolar impedance, unipolar electrical activity, bipolar electrical activity, and temperature. For example, the processing circuitry 74 may use the pre-treatment, in-treatment, and post-treatment data to determine post-ablation (post-treatment) changes in tissue impedance due to the ice thaw, post-ablation (post-treatment) changes in electrical activity, and post-ablation (post-treatment) changes in pace thresholds. The processing circuitry 74 may compare pre-treatment data to in-treatment and/or post-treatment data to identify tissue locations in which optimal or sufficient lesion formation has occurred and tissue locations in which inadequate, incomplete, or insignificant lesion formation has occurred. The processing circuitry 74 may be configured to correlate the ice thickness between the treatment element and the tissue and/or the amount of ice formation between mapping electrodes to a quality of lesion formation in the tissue. For example, the processing circuitry may establish a threshold ice ball thickness (such as an ice thickness of between 3 mm and 4 mm). If the processing circuitry 74 determines that the ice ball has a thickness greater than the threshold thickness, the processing circuitry 74 may determine that a transmural lesion has been formed in the tissue. If the processing circuitry 74 determines the lesion is transmural, the system may alert the user that no further treatment time is needed.

In a further non-limiting example, the processing circuitry 74 may compare pre-treatment pace threshold to post-treatment pace threshold to determine whether ablation of the myocardial tissue has occurred. For example, the processing circuitry 74 may establish a threshold difference between the pre-treatment and post-treatment pace threshold measurements at which sufficient ablation (lesion formation) is deemed to have occurred. If the post-treatment pace threshold measurements are greater than the pre-treatment pace threshold measurements by an amount at least equal to the threshold difference, the processing circuitry may determine that the area of tissue in contact with the treatment element has been ablated. For example, the threshold pace difference may be an amount that is approximately three-fold to five-fold greater than the pre-treatment pace threshold amount. In a further non-limiting example, the processing circuitry 74 may compare pre-treatment, in-treatment, and post-treatment unipolar impedance to determine a maximum ice thickness and to monitor the progress of ice thaw after ablation (that is, once the circulation of cryogenic fluid through the treatment element has ended). In a further non-limiting example, the processing circuitry 74 may compare pre-treatment, in-treatment, and post-treatment bipolar impedance measurements to determine ice thickness between mapping electrodes 40. In a further non-limiting example, the processing circuitry 74 may compare pre-treatment, in-treatment, and post-treatment unipolar impedance measurements, and/or pre-treatment, in-treatment, and post-treatment bipolar impedance measurements, to determine lesion formation and, therefore, treatment efficacy. The impedance value(s) that may indicate sufficient lesion formation may be based on parameters such as the surface area of the mapping electrodes 40 and tissue contact quality.

In a further non-limiting example, the processing circuitry 74 may compare pre-treatment impedance to post-treatment impedance measurements between electrodes to determine an extent of lesion formation, that is, surface area, of a lesion. The processing circuitry 74 may compare pre-treatment and post-treatment data for each mapping electrode 40 to identify which mapping electrodes 40 have recorded an increase in impedance that indicates sufficient lesion formation has occurred. For example, the processing circuitry 74 may use pre-treatment impedance data to establish or determine a baseline impedance value for each mapping electrode 40. The processing circuitry 74 may then use the in-treatment impedance data to determine the electrical activity and/or the pacing threshold increase on each of the mapping electrodes 40 that was in contact with the tissue to define the area that was sufficiently ablated and to demarcate the ablated tissue on the 3D anatomical map. Finally, the mapping circuitry 74 may correlate the location(s) of mapping electrodes 40 deemed to be associated with sufficient lesion formation to create a map or display of the lesion. This data, and the map or display created from it, may then be used by the processing circuitry 74 and/or the user to automatically or manually determine the surface area (size) of the lesion. In one embodiment, the processing circuitry 74 may be configured to determine, for each mapping electrode 40, that at least a portion of the area of tissue proximate that mapping electrode 40 has been ablated when the mapping electrode 40 records a post-treatment electrogram amplitude value of 0.5 mV or less, and the processing circuitry 74 may further be configured to determine a lesion surface area based on the post-treatment electrogram amplitude recorded by each of the plurality of mapping electrodes 40. Put another way, the processing circuitry 40 may be configured to determine whether each mapping electrode 40 is in contact with or proximate a portion of an area of tissue that has been sufficiently ablated. Then, a surface area may be calculated, and a surface area map created, by connecting mapping electrode 40 locations that are associated with lesion formation.

Further, in an optional ninth step 190, the navigation system 16 may receive data from the mapping electrodes 40 and sensors 42 and/or from the control unit 14, and the navigation system processing circuitry 82 may process the data to generate a map of at least a portion of the heart (or other treatment area). The map may display areas of the treatment location in which optimal or sufficient lesion formation has occurred 94 and areas of the treatment location in which inadequate, incomplete, or insignificant lesion formation has occurred 96. This map may be displayed to the user, who may then use the information to reposition the device 12 to ablate or further ablate areas in which optimal or sufficient lesion formation has not yet occurred.

Although the method shown in FIG. 7 includes the recording of pre-treatment, in-treatment, and post-treatment data, and the comparison of that data, it will be understood that in some embodiments the method includes recording and comparing only pre-treatment and post-treatment data, only pre-treatment and in-treatment data, or only in-treatment and post-treatment data. Further, data may be continuously recorded during the entire procedure. Therefore, pre-treatment data may become in-treatment data, and in-treatment data may become post-treatment data, without a clear delineation. Thus, although not explicitly shown in FIG. 7, it will be understood that data may be continuously recorded throughout the entire procedure, even though individual steps are shown. Additionally, it will be understood that in some embodiments the processing circuitry 74 does not generate or display a map of lesion formation.

Figure 8:
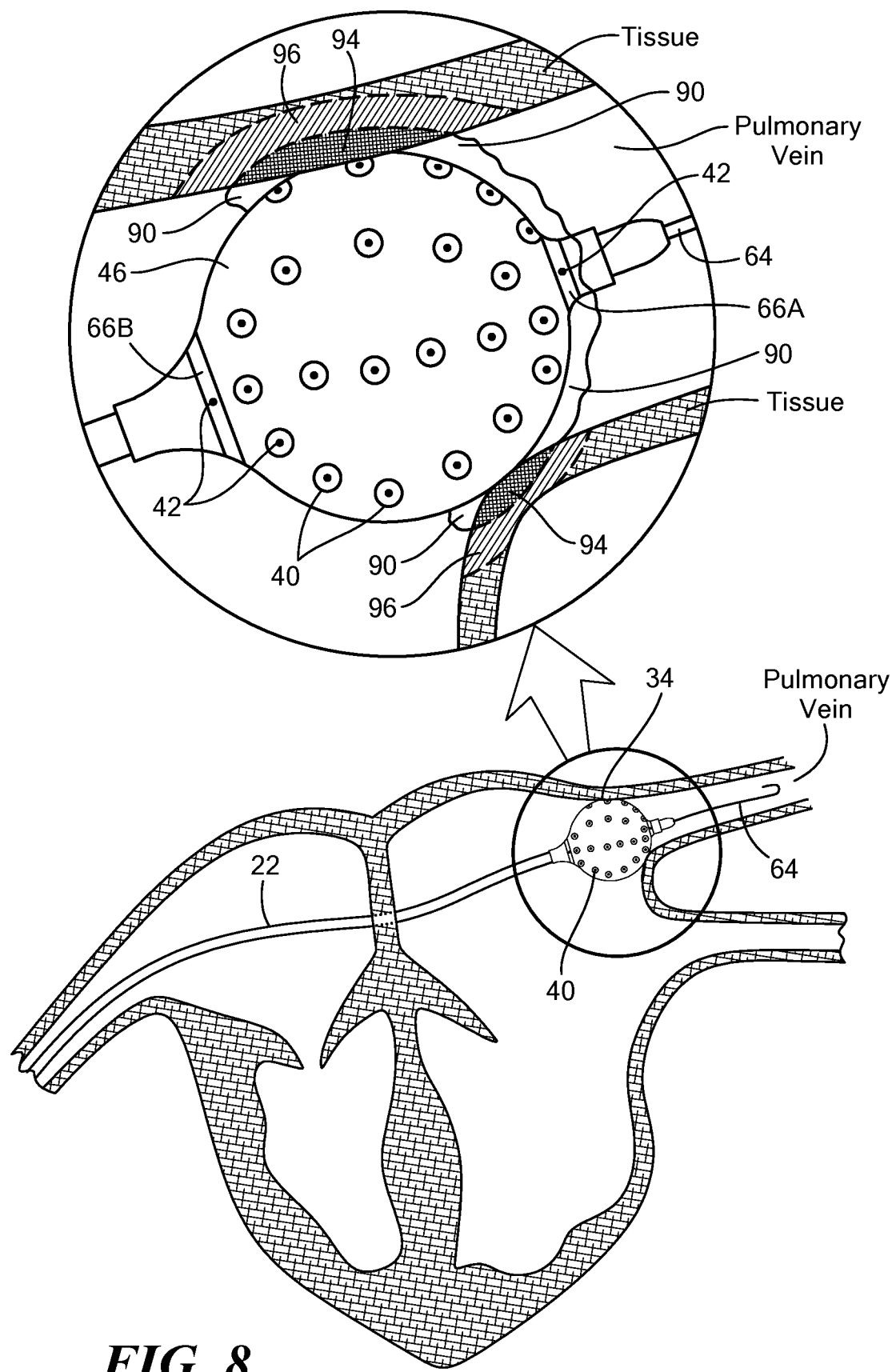
FIG. 8 shows a treatment element of the medical device in contact with a pulmonary vein ostium.
Figure 9:
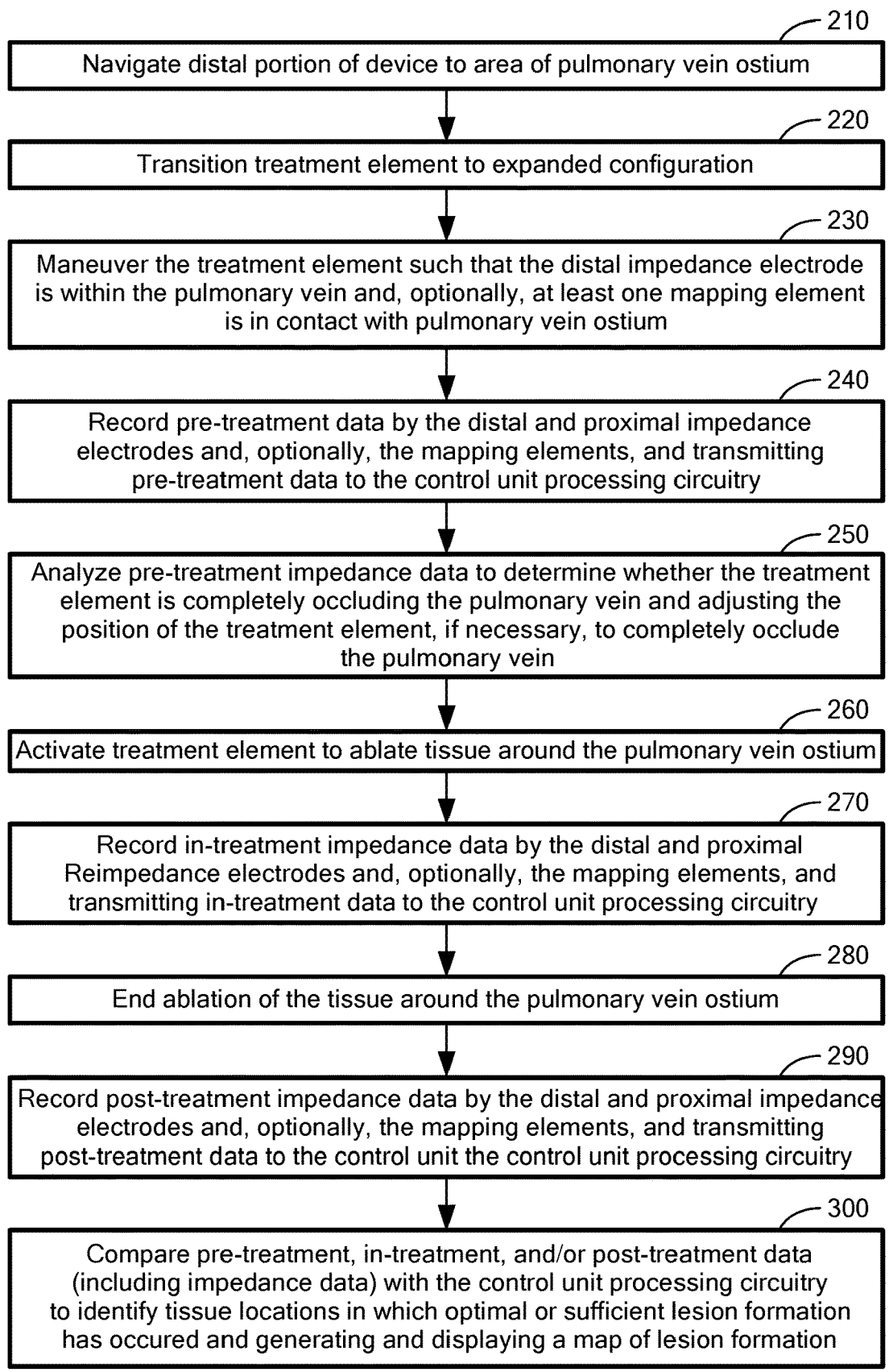
FIG. 9 shows an exemplary method of use of the medical device for determining pulmonary vein occlusion.
Figure 10:
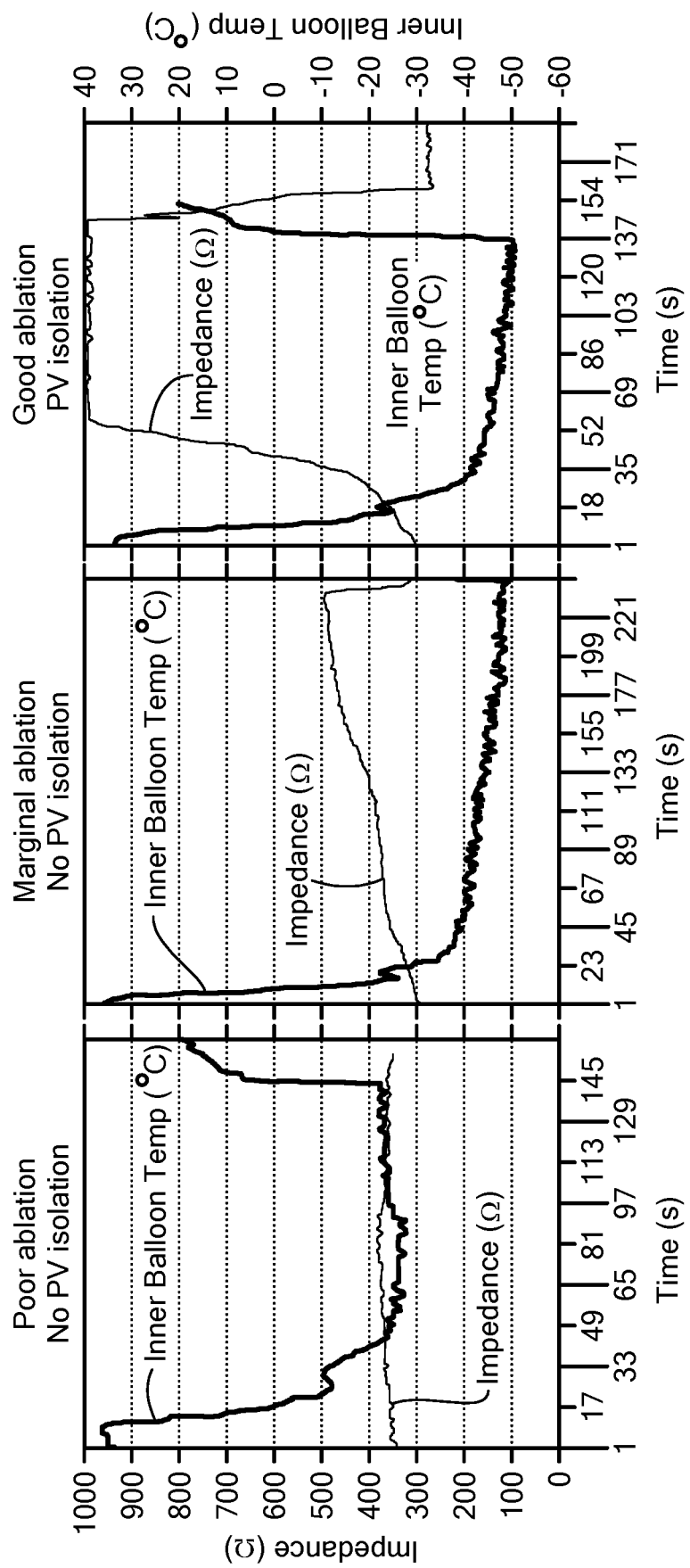
FIG. 10 shows a graph illustrating a correlation between temperature, time, and impedance during pulmonary vein isolation.

Referring now to FIGS. 8-10, an embodiment of a medical device positioned at and in contact with a pulmonary vein ostium is shown. FIG. 10 shows a chart correlating impedance, time, and temperature to pulmonary vein occlusion and ablation (isolation). As used herein, the term "PV tissue" or "pulmonary vein tissue" may include tissue of the PV ostium, the PV antrum, LA wall tissue, and/or tissue at the junction between the LA and PV, and is not limited to tissue within the PV. In fact, ablation of tissue within the PV may be undesirable. In a first step 210, the distal portion 28 of the device 12 may be navigated to a target treatment location, such as at or proximate a pulmonary vein ostium. The treatment location may be accessed through a femoral, radial, or brachial location. In a second step 220, the treatment element 34 may be transitioned from an at least substantially linear first configuration to an expanded second configuration. For example, cryogenic fluid may be delivered from the source of cryogenic fluid through the fluid delivery conduit 60, fluid injection element 48, and into the interior chamber 36 to inflate the inner 44, and expand the outer 46, cryoballoon (this expansion of the outer cryoballoon 46 may also be referred to as inflating the outer cryoballoon 46).

In a third step 330, the expanded treatment element 34 may be maneuvered or positioned such the distal impedance electrode 66A is located within the pulmonary vein. Optionally, the expanded treatment element 34 also may be maneuvered such that at least one mapping electrode 40 is in contact with tissue, such as tissue surrounding the pulmonary vein ostium. The user may use position information from the impedance electrodes 66 and/or the imaging system 18 to assist with placement of the treatment element 34. The expanded treatment element 34 may be positioned at the pulmonary vein (PV) ostium to occlude the PV, or block the flow of blood from the PV into the left atrium (LA) of the heart. Occlusion of the PV not only serves to position the treatment element 34 to create a circumferential lesion around the PV ostium, but also prevents warm blood from flowing over the portions of the treatment element 34 that are (or should be) in contact with the target tissue, thereby enhancing the ability of the treatment element 34 to reach sufficiently cold temperatures for creating permanent, and circumferential, cryoablation lesions on or in the target tissue. The blocked blood within the PV may be referred to as "stagnant" blood, whereas the blood within the LA may be referred to as "flowing" blood, as blood may still enter the LA from the other three PVs that are not being occluded by the catheter 12. Cold saline solution may be delivered from the distal portion of the device 12, such as through the guidewire lumen 62 or other fluid delivery orifice, into the blood within the PV. Impedance and temperature data from the first or distal impedance electrode 66A and temperature sensors or thermocouple 42 associated with the distal impedance electrode 66A, respectively, may be used to evaluate PV occlusion by, and position of, the treatment element 34. The temperature recovery profile may define whether the treatment element 34 is adequately occluding the PV. If the PV is not completely occluded, blood flow past the treatment element 34 may have the effect of raising the temperature of the treatment element 34. If blood is flowing past the treatment element 34, the temperature recorded by the temperature sensor 42 associated with the distal impedance electrode 66A will increase faster than it would if the PV were completely occluded and the cold saline solution were delivered into stagnant blood.

The impedance electrodes 66A, 66B may also be used to evaluate occlusion of a body lumen by the treatment element 34, such as a pulmonary vein. Further, the mapping electrodes 40 may be used for anatomical high-resolution chamber definition (such as by collecting high-density anatomical and electrical activity from the tissue), high-fidelity electrical activation mapping and electrical amplitude determination of the cardiac chamber, pacing and pace threshold determination, rapid activation maps (such as by recording electrical activity throughout the heart by moving the treatment element 34 relative to the cardiac tissue), pre-treatment, in-treatment, and post-treatment impedance determination to define tissue viability, effective ablation associated with ice formation and thickness determinations, and post-treatment efficacy, further defined by local electrogram activity and pace threshold changes. Additionally, the treatment element 34 may be used for not only cryoablation, but also for cold mapping.

In a fourth step 240, pre-treatment data may be recorded by and transmitted from the impedance electrodes 66A, 66B, mapping electrode(s) 40, and/or sensor(s) 42 to the control unit processing circuitry 74 for further processing and communication to the user. This pre-treatment data may provide baseline or threshold values to which in-treatment and post-treatment data may be compared to evaluate treatment efficacy. For example, pre-treatment impedance data from the impedance electrodes 66A, 66B and temperature data from the temperature sensors 42, particularly data from the first or distal impedance electrode 66A and its associated temperature sensor 42, may be used to determine the quality of occlusion of the pulmonary vein by the treatment element 34 in a later step by its comparison to in-treatment and/or post-treatment data. As a further example, the mapping electrodes 40 may be configured to record pre-treatment tissue impedance, pre-treatment local electrical activity, and pre-treatment pace threshold. The mapping electrodes 40 may operate as a unipolar and bipolar electrode array, configured to record local electrograms (unipolar and/or bipolar), a unipolar pace threshold, and impedance (unipolar and/or bipolar). Likewise, the sensors 42 may be configured to record pre-treatment temperature measurements.

Additionally, temperature data from the temperature sensors or thermocouple 42 associated with the distal impedance electrode 66A may be used to evaluate PV occlusion by, and position of, the treatment element 34, as discussed above. For example, as shown in FIG. 10, comparison of in-treatment and/or post-treatment temperature data to pre-treatment temperature data may indicate whether the PV is being or has been completely isolated. In a fifth step 250, the pre-treatment may be used to determine whether the device 12 is properly positioned at the PV ostium and, if not, the device 12 may be repositioned as needed.

In a sixth step 260, the treatment element 34 may be activated to ablate the target tissue. For example, the target tissue may be cryoablated by circulating cryogenic fluid through the treatment element 34 to cool the outer cryoballoon 46 to a temperature sufficient to ablate tissue with which it is in contact. Additionally, if the device 12 includes one or more treatment elements in addition to the cryoballoons 44, 46, the device 12 may also be used to ablate the target tissue through one or more energy modalities, such as by delivering radiofrequency energy, ultrasound energy, laser energy, or by other energetic transfer with the tissue.

In a seventh step 270, in-treatment data may be collected by the impedance electrodes 66A, 66B, mapping electrodes 40, and/or sensors 42 while the treatment element(s) 34 is activated and ablating the target tissue, and this data may be transmitted from the impedance electrodes 66A, 66B, mapping electrode(s) 40 and/or sensors 42 to the control unit processing circuitry 74 for further processing and communication to the user. For example, the impedance electrodes 66A, 66B may record impedance measurements (for example, high-resolution impedance measurements), the mapping electrodes 40 may record impedance measurements (for example, high-resolution impedance measurements), and the sensors 42 may record temperature measurements from the tissue. These measurements may then be transmitted to the control unit 14, where the processing circuitry 74 may process use them to determine the size (surface area) of the tissue lesion created by the treatment, areas of sufficient lesion formation, and/or a thickness of ice formation. Further, in-treatment impedance measurements from the impedance electrodes 66A, 66B and in-treatment temperature measurements form the sensor(s) 42 may be continuously recorded during the ablation phase and compared to each other to evaluate occlusion of the PV and, therefore, lesion creation in the tissue surrounding the PV ostium. As discussed above, if the PV is not completely occluded, blood flow past the treatment element 34 may have the effect of raising the temperature of the treatment element 34, possibly resulting in the formation of reversible lesions on or in the target tissue. Additionally, good occlusion of the PV may also be indicated by a significant increase in impedance (for example, as shown in FIG. 10). Ice formation over the first or distal impedance electrode 66A (for example, as shown in FIG. 8) may cause increased impedance values as measured by the first impedance electrode 66A, As the outer cryoballoon 46 is cooled to ablate the tissue, ice 90 from freezing blood surrounding the treatment site may form between the cryoballoon 46 and the tissue and cryoadhere the treatment element to the tissue. This ice 90 may contribute to lesion formation; therefore, assessment of the thickness of the ice may provide an indication of lesion quality and treatment efficacy and may help prevent injury to non-target tissues, such as the esophagus, lungs, and phrenic nerve. For example, the processing circuitry may establish a threshold ice thickness that indicates sufficient circumferential lesion formation in the tissue surrounding the pulmonary vein, such as by using a data table of empirical evidence or historical data for a particular patient. As ice thickness increases, the mapping electrodes 40 may detect a rise in impedance.

In an eighth step 280, circulation of cryogenic fluid within the treatment element 34 may be stopped, either manually or automatically by the system 10, in order to end the ablation of the tissue, allow the ice 90 to thaw, and to break cryoadhesion between the treatment element (i.e. the cryoballoon 46) and the tissue. In a ninth step 290, post-treatment data may be transmitted from the mapping electrode(s) 40 and the sensors 42 to the control unit processing circuitry 74 for further processing and communication to the user. Post-treatment data may include, but is not limited to, unipolar pace threshold, unipolar impedance, bipolar impedance, and temperature. For example, the processing circuitry 74 may use the pre-treatment, in-treatment, and post-treatment data to determine post-ablation (post-treatment) ablation efficacy, such as that indicated by changes in tissue impedance due to the ice thaw, post-ablation (post-treatment) changes in electrical activity, and post-ablation (post-treatment) changes in pace thresholds. The processing circuitry 74 may compare pre-treatment data to in-treatment and/or post-treatment data to identify tissue locations in which optimal or sufficient lesion formation has occurred and tissue locations in which inadequate, incomplete, or insignificant lesion formation has occurred. The processing circuitry 74 may be configured to correlate the ice thickness between the treatment element and the tissue and/or the amount of ice formation between mapping electrodes to a quality of lesion formation in the tissue. For example, the processing circuitry may establish a threshold ice ball thickness (such as an ice thickness of between 3 mm and 4 mm). If the processing circuitry 74 determines that the ice ball has a thickness greater than the threshold thickness, the processing circuitry 74 may determine that a transmural lesion has been formed in the tissue. If the processing circuitry 74 determines the lesion is transmural, the system may alert the user that no further treatment time is needed.

In a further non-limiting example, the processing circuitry 74 may compare pre-treatment pace threshold to post-treatment pace threshold to determine whether ablation of the myocardial tissue has occurred. For example, the processing circuitry 74 may establish a threshold difference between the pre-treatment and post-treatment pace threshold measurements at which sufficient ablation (lesion formation) is deemed to have occurred. If the post-treatment pace threshold measurements are greater than the pre-treatment pace threshold measurements by an amount at least equal to the threshold difference, the processing circuitry may determine that the area of tissue in contact with the treatment element has been ablated. For example, the threshold pace difference may be an amount that is approximately three-fold to five-fold greater than the pre-treatment pace threshold amount. In a further non-limiting example, the processing circuitry 74 may compare pre-treatment, in-treatment, and post-treatment unipolar impedance to determine a maximum ice thickness and to monitor the progress of ice thaw after ablation (that is, once the circulation of cryogenic fluid through the treatment element has ended). In a further non-limiting example, the processing circuitry 74 may compare pre-treatment, in-treatment, and post-treatment bipolar impedance measurements to determine ice thickness between mapping electrodes. In a further non-limiting example, the processing circuitry 74 may compare pre-treatment, in-treatment, and post-treatment unipolar impedance measurements, and/or pre-treatment, in-treatment, and post-treatment bipolar impedance measurements, to determine lesion formation and, therefore, treatment efficacy. More importantly, the elimination or significant reduction in post-treatment local electrogram amplitude over pre-treatment local electrogram amplitude to a value of approximately 0.5 mV or less may indicate sufficient ablation has occurred. For example, a bipolar impedance increase of approximately 500 ohms (±50 ohms) may indicate sufficient ablation (lesion formation) has occurred.

Further, in an optional tenth step 300, the navigation system 16 may receive data from the mapping electrodes 40 and sensors 42 and/or from the control unit 14, and the navigation system processing circuitry 82 may process the data to generate a map of at least a portion of the heart (or other treatment area). The map may display areas of the treatment location in which optimal or sufficient lesion formation has occurred 94 and areas of the treatment location in which inadequate, incomplete, or insignificant lesion formation has occurred 96. This map may be displayed to the user, who may then use the information to reposition the device 12 to ablate or further ablate areas in which optimal or sufficient lesion formation has not yet occurred. As a non-limiting example, the map and/or data may be used to determine whether a complete circumferential lesion has been created around the PV ostium.

Although the method shown in FIG. 9 includes the recording of pre-treatment, in-treatment, and post-treatment data, and the comparison of that data, it will be understood that in some embodiments the method includes recording and comparing only pre-treatment and post-treatment data, only pre-treatment and in-treatment data, or only in-treatment and post-treatment data. Further, data may be continuously recorded during the entire procedure. Therefore, pre-treatment data may become in-treatment data, and in-treatment data may become post-treatment data, without a clear delineation. Thus, although not explicitly shown in FIG. 9, it will be understood that data may be continuously recorded throughout the entire procedure, even though individual steps are shown. Additionally, it will be understood that in some embodiments the processing circuitry 74 does not generate or display a map of lesion formation.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system for treating an area of tissue, the system comprising:
    a medical device including:
        an elongate body having a distal portion, a proximal portion, and a distal tip;
        an expandable treatment element disposed on the distal portion of the elongate body, the expandable treatment element having an inner surface and an opposite outer surface, the outer surface of the expandable treatment element defining a proximal face and a distal face opposite the proximal face;
        a shaft having a first portion and a second portion, the first portion of the shaft being disposed within the expandable treatment element and the second portion of the shaft being disposed outside of the expandable treatment element and proximate the distal tip;
        a first plurality of electrodes, each electrode from the first plurality of electrodes having a proximal portion and a distal portion opposite the proximal portion, at least one of the first plurality of electrodes being disposed on the distal portion of the elongate body and the distal portion of the electrode from the first plurality of electrodes being located immediately adjacent to and in contact with the proximal face of the expandable treatment element, the first plurality of electrodes being configured to record and transmit to a processing circuitry a first recording of a pace threshold prior to a treatment of the tissue and a second recording of the pace threshold after the treatment of the tissue;
        a second plurality of electrodes, each electrode from the second plurality of electrodes having a proximal portion and a distal portion opposite the proximal portion, at least one of the second plurality of electrodes being disposed on the second portion of the shaft and the proximal portion of the electrode from the second plurality of electrodes being located immediately adjacent to and in contact with the distal face of the expandable element, the second plurality of electrodes being configured to record and transmit to the processing circuitry a third recording of the pace threshold prior to the treatment of the tissue and a fourth recording of the pace threshold after the treatment of the tissue, the first and the second plurality of electrodes further including:
        a plurality of mapping electrodes on the expandable treatment element, the plurality of mapping electrodes configured to record and transmit to the processing circuitry a fifth recording of the pace threshold prior to the treatment of the tissue and a sixth recording of the pace threshold after the treatment of the tissue; and
    a control unit including:
        a cryogenic fluid source in fluid communication with the expandable treatment element, circulation of the cryogenic fluid within the expandable treatment element causing formation of an ice ball between the expandable treatment element and the area of tissue; and
        processing circuitry in electrical communication with the first plurality of electrodes, the second plurality of electrodes, and the plurality of mapping electrodes,
        the processing circuitry configured to compare the first recording, the second recording, the third recording, the fourth recording, the fifth recording and the sixth recording to determine lesion quality.

2. The medical system of claim 1, wherein the medical device further includes a plurality of sensors on the expandable treatment element, each of the plurality of sensors being associated with at least one of the plurality of mapping electrodes.

3. The medical system of claim 2, wherein each of the plurality of mapping electrodes includes a corresponding one of the plurality of sensors.

4. The medical system of claim 3, wherein each of the plurality of mapping electrodes is further configured to record from the area of tissue at least one of unipolar impedance measurements, bipolar impedance measurements, local electrical activity, and pace threshold measurements before, during, and after circulation of the cryogenic fluid within the expandable treatment element, and each of the plurality of sensors is a plurality of temperature sensors configured to record temperature measurements before, during, and after circulation of the cryogenic fluid within the expandable treatment element.

5. The medical system of claim 4, wherein the processing circuitry is configured to receive recordings from the plurality of mapping electrodes and configured to determine, for each of the plurality of mapping electrodes:
that at least a portion of the area of tissue proximate the mapping electrode has been ablated when the mapping electrode records a post-treatment electrogram amplitude value of 0.5 mV or less,
the processing circuitry being further configured to determine a lesion surface area based on the post-treatment electrogram amplitude recorded by each of the plurality of mapping electrodes.

6. The medical system of claim 4, wherein the processing circuitry is configured to receive recordings from the plurality of mapping electrodes and to:
compare unipolar impedance measurements recorded before the circulation of cryogenic fluid within the expandable treatment element to unipolar impedance measurements recorded after the circulation of cryogenic fluid within the expandable treatment element has ended;
determine a thickness of the ice ball between the expandable treatment element and the area of tissue based on the comparison of the unipolar impedance measurements; and
correlate the thickness of the ice ball to a lesion quality.

7. The medical system of claim 6, wherein the processing circuitry is further programmed to:
compare bipolar impedance measurements recorded before the circulation of cryogenic fluid within the expandable treatment element to bipolar impedance measurements recorded after the circulation of cryogenic fluid within the expandable treatment element has ended;
quantify a formation of ice between a pair of expandable treatment elements used to record the bipolar impedance measurements based on the comparison of the bipolar impedance measurements; and
correlate the formation of ice to a lesion quality.

8. The medical system of claim 6, wherein the processing circuitry is further programmed to:
compare pace threshold measurements recorded before the circulation of cryogenic fluid within the expandable treatment element to pace threshold measurements recorded after the circulation of cryogenic fluid within the expandable treatment element has ended; and
determine whether the area of tissue has been ablated based on the comparison.

9. The medical system of claim 8, wherein the processing circuitry is configured to determine that the area of tissue has been ablated when the pace threshold measurements recorded after the circulation of cryogenic fluid within the expandable treatment element has ended are greater than the pace threshold measurements recorded before the circulation of cryogenic fluid within the expandable treatment element by more than a threshold difference.

10. The medical system of claim 1, wherein each electrode from the first and second plurality of electrodes has a width of approximately 0.5 mm.

11. The medical system of claim 10, wherein each of the first and second impedance electrodes are configured to record unipolar impedance measurements and bipolar impedance measurements, the processing circuitry further being configured to determine a thickness of the ice ball between the area of tissue and at least the first impedance electrode based on at least one of unipolar and bipolar impedance measurements recorded by at least the first impedance electrode.

12. The medical system of claim 1, wherein the medical device has a longitudinal axis, the plurality of mapping electrodes being arranged in a plurality of linear formations, each of the plurality of linear formations being at least substantially parallel to the longitudinal axis.

13. The medical system of claim 12, wherein each of the plurality of linear formations of mapping electrodes extends between the distal face and the proximal face of the expandable treatment element.

14. The medical system of claim 1, wherein the medical device has a longitudinal axis, the plurality of mapping electrodes being arranged in a plurality of bands, each of the plurality of bands at least partially extending around the longitudinal axis.

15. The medical system of claim 1, wherein the plurality of mapping electrodes are arranged in clusters of two or more mapping electrodes.

16. The medical system of claim 1, wherein the plurality of mapping electrodes are randomly arranged on the expandable treatment element.

17. A medical system for treating an area of tissue, the system comprising:
a medical device including:
an elongate body having a distal portion, a proximal portion, and a distal tip;
an expandable treatment element disposed on the distal portion of the elongate body, the expandable element having an inner surface and an opposite outer surface, the outer surface of the expandable treatment element defining a proximal face and a distal face opposite the proximal face;
a shaft having a first portion and a second portion, the first portion of the shaft being disposed within the expandable treatment element and the second portion of the shaft being disposed outside of the expandable treatment element and proximate the distal tip;
a plurality of mapping electrodes on the expandable treatment element, each of the plurality of mapping electrodes being configured to record from the area of tissue at least one of unipolar impedance measurements, bipolar impedance measurements, local electrical activity, and pace threshold measurements before, during, and after circulation of a cryogenic fluid within the expandable treatment element;
a plurality of temperature sensors on the expandable treatment element, each of the plurality of temperature sensors being associated with at least one of the plurality of mapping electrodes, each of the plurality of temperature sensors being configured to record from the area of tissue temperature measurements before, during, and after circulation of the cryogenic fluid within the expandable treatment element;
a first impedance electrode having a proximal portion and a distal portion opposite the proximal portion, the first impedance electrode being disposed on the second portion of the shaft and the proximal portion of the first impedance electrode being located immediately adjacent to and in contact with the distal face of the expandable treatment element, the first impedance electrode including a distal temperature sensor; and a second impedance electrode having a proximal portion and a distal portion opposite the proximal portion, the second impedance electrode being disposed on the distal portion of the elongate body and the distal portion of the second impedance electrode being located immediately adjacent to and in contact with the proximal face of the expandable treatment element, the second impedance electrode including a distal temperature sensor, each of the first and second impedance electrodes having a width of approximately 0.5 mm; and a control unit including:

a cryogenic fluid source in fluid communication with the expandable treatment element, circulation of the cryogenic fluid within the expandable treatment element causing formation of an ice ball between the expandable treatment element and the area of tissue; and processing circuitry in electrical communication with the plurality of mapping electrodes, the plurality of sensors, the first and second impedance electrodes, and the distal and proximal temperature sensors, the processing circuitry being configured to determine transmurality of a lesion based on signals received from the plurality of mapping electrodes by at least one of:

comparing unipolar impedance measurements recorded before the circulation of cryogenic fluid within the expandable treatment element to at least one of unipolar impedance measurements recorded during the circulation of cryogenic fluid within the expandable treatment element and unipolar impedance measurements recorded after the circulation of cryogenic fluid within the expandable treatment element has ended;

comparing bipolar impedance measurements recorded before the circulation of cryogenic fluid within the expandable treatment element to at least one of bipolar impedance measurements recorded during the circulation of cryogenic fluid within the expandable treatment element and bipolar impedance measurements recorded after the circulation of cryogenic fluid within the expandable treatment element has ended;

comparing pace threshold measurements recorded before the circulation of cryogenic fluid within the expandable treatment element to at least one of pace threshold measurements recorded during the circulation of cryogenic fluid within the treatment element and pace threshold measurements recorded after the circulation of cryogenic fluid within the expandable treatment element has ended; and comparing electrogram amplitude measurements recorded before the circulation of cryogenic fluid within the expandable treatment element to at last one of electrogram amplitude measurements recorded during the circulation of cryogenic fluid within the expandable treatment element and electrogram amplitude measurements recorded after the circulation of cryogenic fluid within the expandable treatment element has ended.

* * * * *